United States Patent [19]
Coss et al.

[11] Patent Number: 5,538,423
[45] Date of Patent: Jul. 23, 1996

[54] APPARATUS FOR CONTROLLING OPERATIONAL PARAMETERS OF A SURGICAL DRILL

[75] Inventors: Ronald G. Coss, Newport Beach; James H. Dabney, Irvine, both of Calif.

[73] Assignee: Micro Motors, Inc., Santa Ana, Calif.

[21] Appl. No.: 158,236

[22] Filed: Nov. 26, 1993

[51] Int. Cl.$^6$ ..................................................... A61C 1/00
[52] U.S. Cl. ............................... 433/27; 433/98; 433/101; 433/106; 433/131; 433/201.1; 408/8; 364/413.28
[58] Field of Search .................................. 433/27, 98, 99, 433/101, 103, 106, 114, 131, 141, 165, 166, 172, 173, 174, 201.1; 408/8, 9, 15, 16; 364/146, 172, 188, 189, 413.01, 413.28, 571.08; 606/80, 104; 318/434, 432; 361/30, 31, 33; 388/815, 809, 900, 909, 937, 816, 821, 822, 823

[56] References Cited

U.S. PATENT DOCUMENTS

| | | | |
|---|---|---|---|
| 3,052,984 | 9/1962 | Mitthauer et al. | 433/106 |
| 4,180,812 | 12/1979 | Kaltenbach et al. | |
| 4,256,998 | 3/1981 | Samuels et al. | |
| 4,305,126 | 12/1981 | Beier et al. | |
| 4,446,456 | 5/1984 | Beier . | |
| 4,479,182 | 10/1984 | Beier . | |
| 4,494,933 | 1/1985 | Matsui | 433/98 |
| 4,526,114 | 7/1985 | Martell et al. | |
| 4,540,318 | 9/1985 | Hornung et al. | 408/9 |
| 4,571,681 | 2/1986 | Beier et al. | |
| 4,622,503 | 11/1986 | Sundblom et al. | |
| 4,713,003 | 12/1987 | Symington et al. | 433/173 |
| 4,723,911 | 2/1988 | Kurtz . | |
| 4,744,752 | 5/1988 | Nakayama et al. | |

(List continued on next page.)

FOREIGN PATENT DOCUMENTS

| | | | |
|---|---|---|---|
| 2645430 | 10/1990 | France | 433/27 |
| 3221146 | 12/1983 | Germany | 433/27 |

OTHER PUBLICATIONS

Brochure, Irrigation Systems, Dyna Dent. (Author unknown, date unknown).
Brochure, Product Catalog, Spectra–Surge, Dentsply/Implant Division, 1993. (Author unknown).
Brochure, Linea Studio, Implantology, Carlo De Giorgi, Nov. 1993.
Brochure, Implantology Surgical Unit, Friedrichsfeld. (Author and date unknown).
Brochure, elcomed Surgical system 100/200, W&H Dentalwerk Bürmoos Ges.m.b.H. (Author and date unknown).
Brochure, Satelec. (Author unknown, date unknown).
Brochure, Physio–Dispenser, Nouvag AG. (Author and date unknown).

*Primary Examiner*—Guy Tucker
*Attorney, Agent, or Firm*—Knobbe, Martens, Olson & Bear

[57] ABSTRACT

The present invention relates to a dental drilling system having a programmable control unit. The control unit controls operating parameters of the drilling system, such as the direction of rotation, the speed of rotation and the torque of a tool bit of a dental drill, as well as the irrigation fluid flow rate generated by a pump and the intensity of light generated by a light source. The control unit can be programmed with a number of sets of data values. Each set of data values represents a desired value for each of the operating parameters to be controlled. Also, each set of data values corresponds to a different step in a dental operation. Thus, for each step of a dental operation, a surgeon can choose a desired set of operating parameter values from those sets that have been preprogrammed. The control unit then controls the operating parameters to achieve and maintain the values represented by the selected set of data values. Also, the control unit determines the electrical current and voltage applied to or generated by the drill motor to calculate the rotation speed and the torque at the tool bit. This enables the control unit to accurately achieve and maintain a specified rotation speed or torque. Applying a predetermined torque to a screw driving bit allows the dental drilling system to be used as a torque wrench.

17 Claims, 23 Drawing Sheets

U.S. PATENT DOCUMENTS

| | | |
|---|---|---|
| 4,758,220 | 7/1988 | Sundblom et al. . |
| 4,859,912 | 8/1989 | Lippmann et al. .................. 315/169.3 |
| 4,878,842 | 11/1989 | Malcmacher et al. ..................... 433/72 |
| 4,893,067 | 1/1990 | Bhagwat et al. ........................ 388/823 |
| 4,983,901 | 1/1991 | Lehmer . |
| 5,014,793 | 5/1991 | Germanton et al. ..................... 173/181 |
| 5,085,586 | 2/1992 | Johnson .................... 433/224 |
| 5,116,168 | 5/1992 | Aihara ..................... 408/9 X |
| 5,235,259 | 8/1993 | Dhindsa et al. ........................ 318/434 |

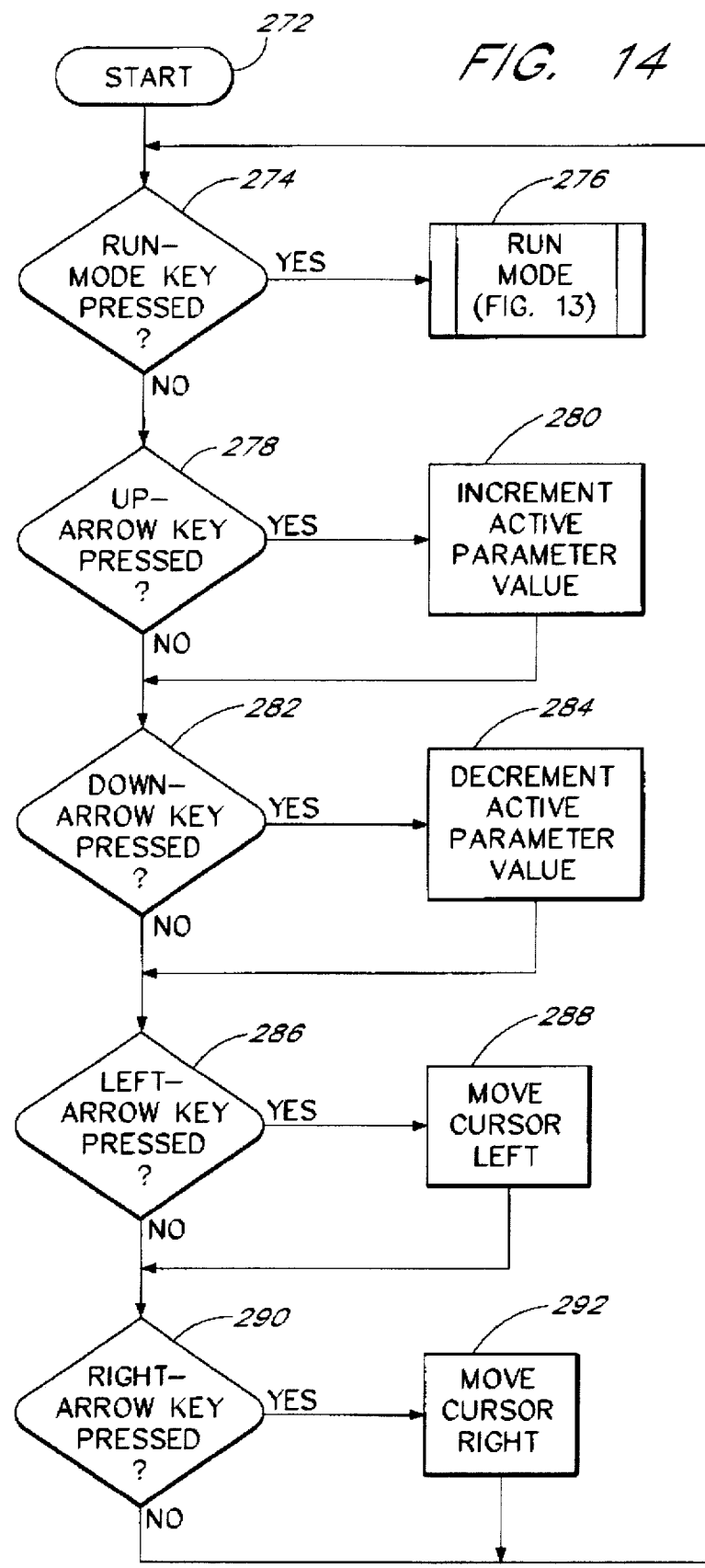

5,538,423

APPARATUS FOR CONTROLLING OPERATIONAL PARAMETERS OF A SURGICAL DRILL

BACKGROUND OF THE INVENTION

1. Field of the Invention

The present invention relates to a method and apparatus for controlling operational parameters of a surgical drilling system for performing a surgical procedure or operation, particularly in the field of oral surgery, and even more particularly in the field of implantology.

2. Background Information

Implantology involves a technique of replacing natural teeth with artificial teeth, where the artificial teeth are secured to the jawbone of the patient. Dental implant operations are usually performed with a dental drilling system comprising a motor controller, a motor and a handpiece, with a gear train and a tool bit. Any of a number of tool bits may be used, such as a drilling bit or a tapping bit.

One step of the procedure involves the use of a drilling bit to drill one or more holes into the jawbone of the patient. The motor controller must be set to drive the motor to rotate the drilling bit at an appropriate speed to drill through the bone. The required motor rotation speed depends on the gear ratio of the gear train of the handpiece.

In a subsequent step of the operation, the surgeon uses the drilling system, along with a tapping bit, to tap the hole(s) in the jawbone. During this step, the rotational speed of the bit must be much slower than that used during the drilling step, so that, when the hole(s) have been completely tapped and the tapping bit bottoms out at the far end of the hole(s), the surgeon can stop the rotation of the tapping bit before the newly-formed threads are stripped by the tapping bit. Frequently, a surgeon finishes the process of tapping the hole(s) by manually operating a hand tapping tool. When using the drilling system to tap the hole(s), the motor speed is coordinated with the gear ratio of the handpiece to generate adequate torque and a suitable rotation speed. After tapping the hole(s), the surgeon screws threaded implant(s) into the threaded hole(s). Implants have a threaded male end for insertion into the threaded hole(s) in the jawbone, and a threaded female end for receiving a screw.

The surgeon now waits for the jawbone to grow back around the male end of the implant(s). After a couple of weeks, one or more tooth fixtures are bolted onto the implant(s) using one or more screws. A tooth fixture may be a single artificial tooth attached to a mounting surface having a hole for receiving the screw, or it may be a plurality of artificial teeth attached to a plate having one or more holes for receiving one or more screws. A screw is placed through a hole in the tooth fixture and driven into the threaded female end of the implant. The screw(s) are preferably driven to a specified torque to ensure a proper attachment of the tooth to the implant. A specially designed torque wrench may be used to achieve the specified torque. An abutment can also be used between an implant and a tooth fixture to ensure that the tooth fixture is mounted at the correct angle. Finally, the screw(s) are covered with a filler.

SUMMARY OF THE INVENTION

The present invention comprises an apparatus for performing a surgical procedure on hard tissue, particularly bone. Such surgical procedure includes a plurality of steps, each of which involves operation of the apparatus in accordance with selected operating parameters. The apparatus comprises a drill comprising a motor, a handpiece, and a tool. Upon activation, the motor drives the tool either directly or indirectly or through a gear train. The apparatus also includes means, such as a keypad, for inputting a first set of data values representing the magnitudes of the operating procedures for one of the plurality of steps of the surgical procedure. Additionally, means, such as the aforesaid keypad, are included for inputting a second set of data values representing the magnitudes of the operating parameters for another of the plurality of steps of the surgical procedure. The first and second sets of data values are stored in storage means, such as an EEPROM. During the surgical procedure, any of the sets of data values can be selectively recalled, and the apparatus operates in accordance with the parameter magnitudes corresponding to the recalled set of data values. At least one selected operational parameter is monitored during operation of the apparatus, and the magnitude of the selected operational parameter is controlled to substantially maintain the magnitude of the selected operational parameter at a magnitude corresponding to the value represented by the recalled set of data values.

In a preferred embodiment, operational parameter monitoring is accomplished by determining the drive voltage applied across the motor and determining the current flowing through the motor. The drive voltage is adjusted to control the magnitude of the selected operational parameter.

Although the present invention is applicable for a number of different types of surgical procedures, the one preferred procedure is oral surgery involving dental implants. In such case, the tool driven by the motor typically comprises a rotating bit; for example, a high speed drilling bit or a tapping bit for tapping threads in the jawbone. In such a dental application, two operating parameters, such as the rotational speed of the bit and the torque on the bit, are preferably maintained at or below a desired maximum value to prevent damage to the handpiece or to the surgical site. In this regard, it will be understood that excessive torque during tapping operations may cause the tapped threads to be stripped when the tapping bit bottoms out in the hole. The torque control of the present invention also permits the handpiece to be used with a screw driver bit to tighten screws without risk of stripping the threads.

In the preferred embodiment, parameters such as torque and speed are limited by controlling the drive voltage so that (a) the magnitudes of these parameters are substantially at or beneath desired maximum values, and (b) the magnitude of at least one of these parameters is substantially at its desired maximum value. The drive voltage may be adjusted in accordance with a selected one of any of four different functions, the selected function depending on which, if any, of the operational parameters have magnitudes that exceed their desired maximum values and which, if any, of the operational parameters have magnitudes that are less than their desired maximum values. Preferably, the drive voltage is supplied to the motor by a switching power regulator utilizing pulse width modulation. The power regulator produces the drive voltage as a function of the pulse width. modulation. The selected one of the four functions is used to control the pulse width modulation, and thereby control the drive voltage on the motor.

An additional aspect of the preferred embodiment includes a device that supplies a DC voltage for lighting a light bulb. The device produces a pulse width modulation signal duty cycle, which increases over time from a minimum to a maximum. This signal is converted to the DC voltage for lighting the light bulb so that the amount of voltage supplied to the light bulb is increased gradually to reduce voltage-induced stress on the filament of the light bulb.

A further aspect of the preferred embodiment includes a brake that rapidly slows motion of the moving tool. The brake comprises a resistance that is connected across the motor to absorb energy of the moving tool.

A further aspect of the present invention includes a method of performing a surgical procedure involving the application of a tool to hard tissue, such as bone. The method comprises the step of inputting into a memory a first set of data values representing magnitudes of operational parameters to be used in one step of the surgical procedure. Also input into the memory is a second set of data values representing magnitudes of operational parameters to be used in another step of the surgical procedure. The first set of data values is recalled from the memory, and the tool is operated using the first set of values. One step of the surgical procedure is then performed by applying the tool to the hard tissue. The second set of values is then recalled from the memory, and the tool is operated in accordance with this second set of values. Another step of the surgical procedure is then performed by applying the tool to the hard tissue. During operation of the tool at least one of the operational parameters is monitored. The operational parameter to be monitored includes at least one of (a) the speed of movement of the tool, and (b) the torque on the tool. The magnitude of the selected operational parameter is controlled in response to the aforesaid monitoring to substantially maintain, during application of the tool, the magnitude of the selected operational parameter that corresponds to the value represented by the data values recalled from the memory.

BRIEF DESCRIPTION OF THE DRAWINGS

FIG. 14 is a flowchart of a system level manual mode program executed by a CPU of the programmable controller of FIG. 5.

DETAILED DESCRIPTION OF THE PREFERRED EMBODIMENT

Figure 1:
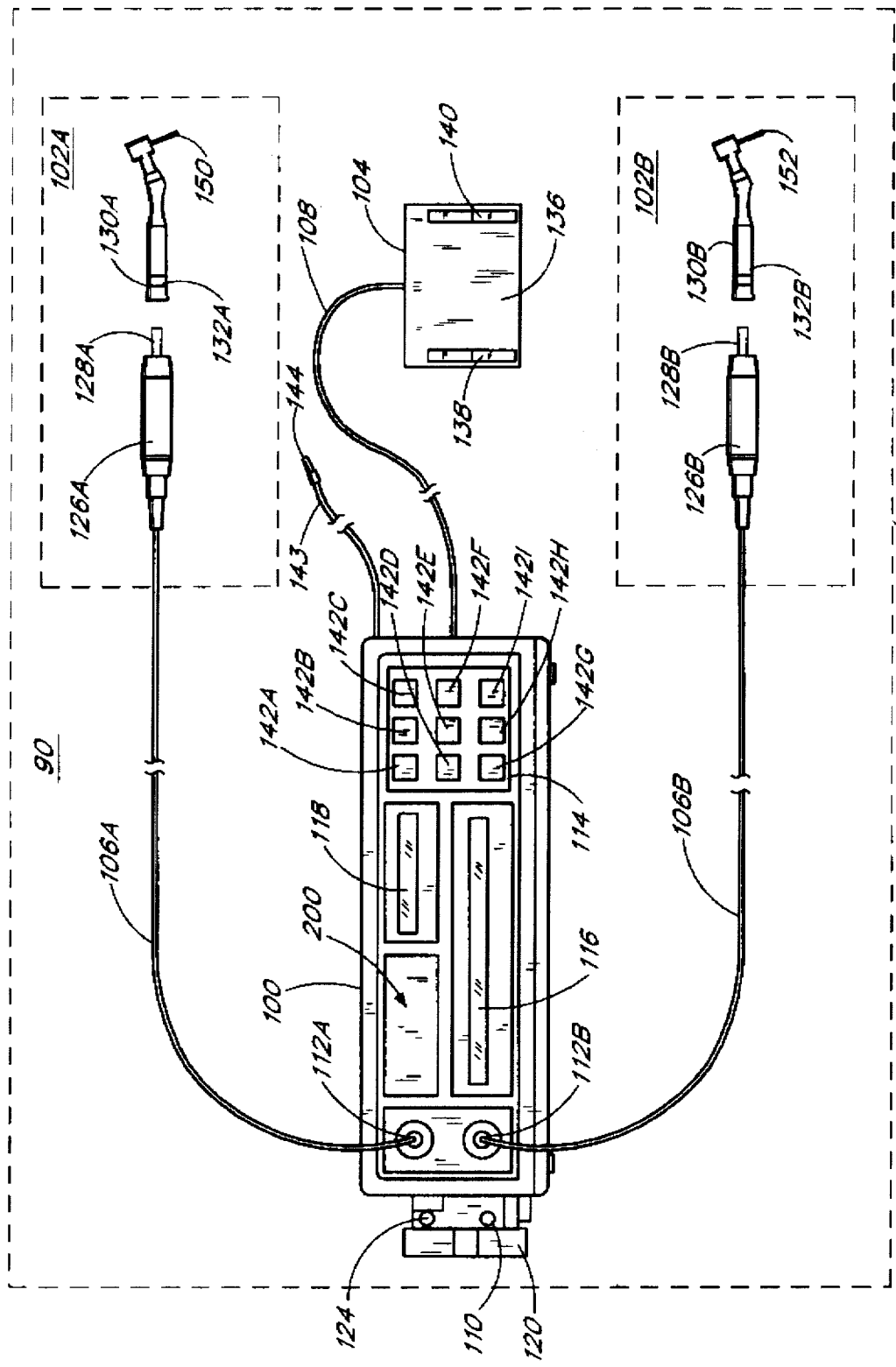
FIG. 1 illustrates a dental drilling system of the present invention comprising two drills, a programmable control unit, a foot switch, and a light source.

FIG. 1 illustrates a preferred embodiment of a dental drilling system 90 of the present invention, which is designed specifically for use in oral surgery applications. The drilling system 90 comprises a programmable control unit 100, a first drill 102A, a second drill 102B, a first drill cable 106A, a second drill cable 106B, a foot switch 104, a foot switch cable 108, a light source 144, a light source cable 143 and a pump 120. The first drill 102A comprises a motor 126A, a shaft 128A and a handpiece 130A. The handpiece 130A comprises a gear train 132A and a drilling bit 150. The second drill 102B comprises a motor 126B, a shaft 128B and a handpiece 130B. The handpiece 130B comprises a gear train 132B and a tapping bit 152.

The programmable control unit 100 comprises a first drill cable connector 112A, a second drill cable connector 112B, a keypad 114, a liquid crystal display (LCD) 116, a light emitting diode (LED) display 118 and a programmable controller 200. The keypad 114 comprises a run-mode key 142A, a program-mode key 142B, a manual-mode key 142C, a skip key 142D, an up-arrow key 142E, a pump on/off key 142F, a left-arrow key 142G, a down-arrow key 142H and a right-arrow key 142I. The foot switch 104 comprises an on/off switch 136, a sequencer switch 138 and a reverse switch 140. The pump 120 comprises an incoming-fluid connector 124 and an outgoing-fluid connector 110.

Figure 2:
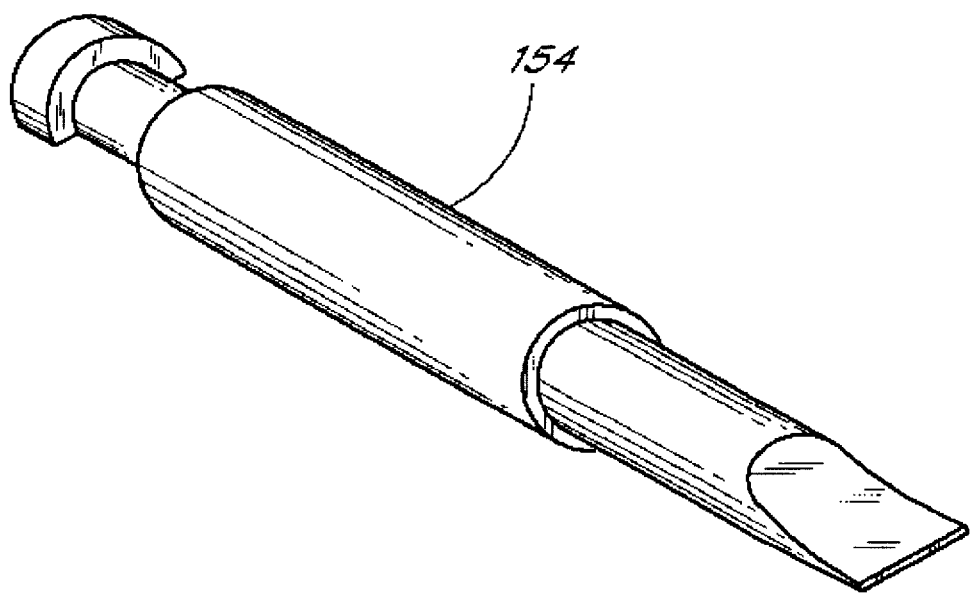
FIG. 2 is a perspective view of a slotted screwdriver bit for use with the drills of FIG. 1.
Figure 3:
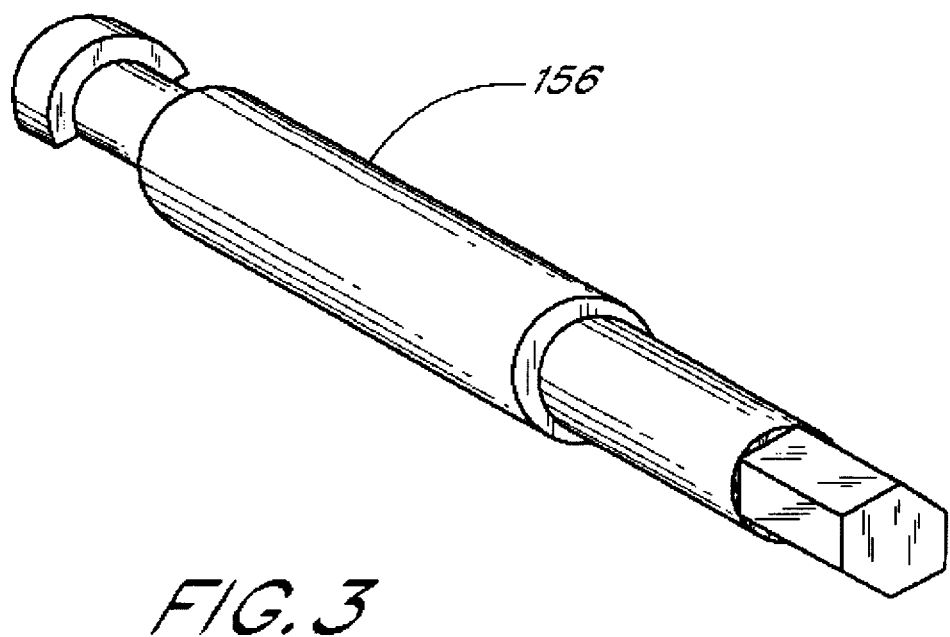
FIG. 3 is a perspective view of a hex screwdriver bit for use with the drills of FIG. 1.

FIG. 2 illustrates a slotted screw driving bit 154 for use with the drills 102A and 102B. FIG. 3 illustrates a hex screw driving bit 156 for use with the drills 102A and 102B. The drilling bit 150, the tapping bit 152, the slotted screw driving bit 154 and the hex screw driving bit 156 constitute tool bits.

Figure 4:
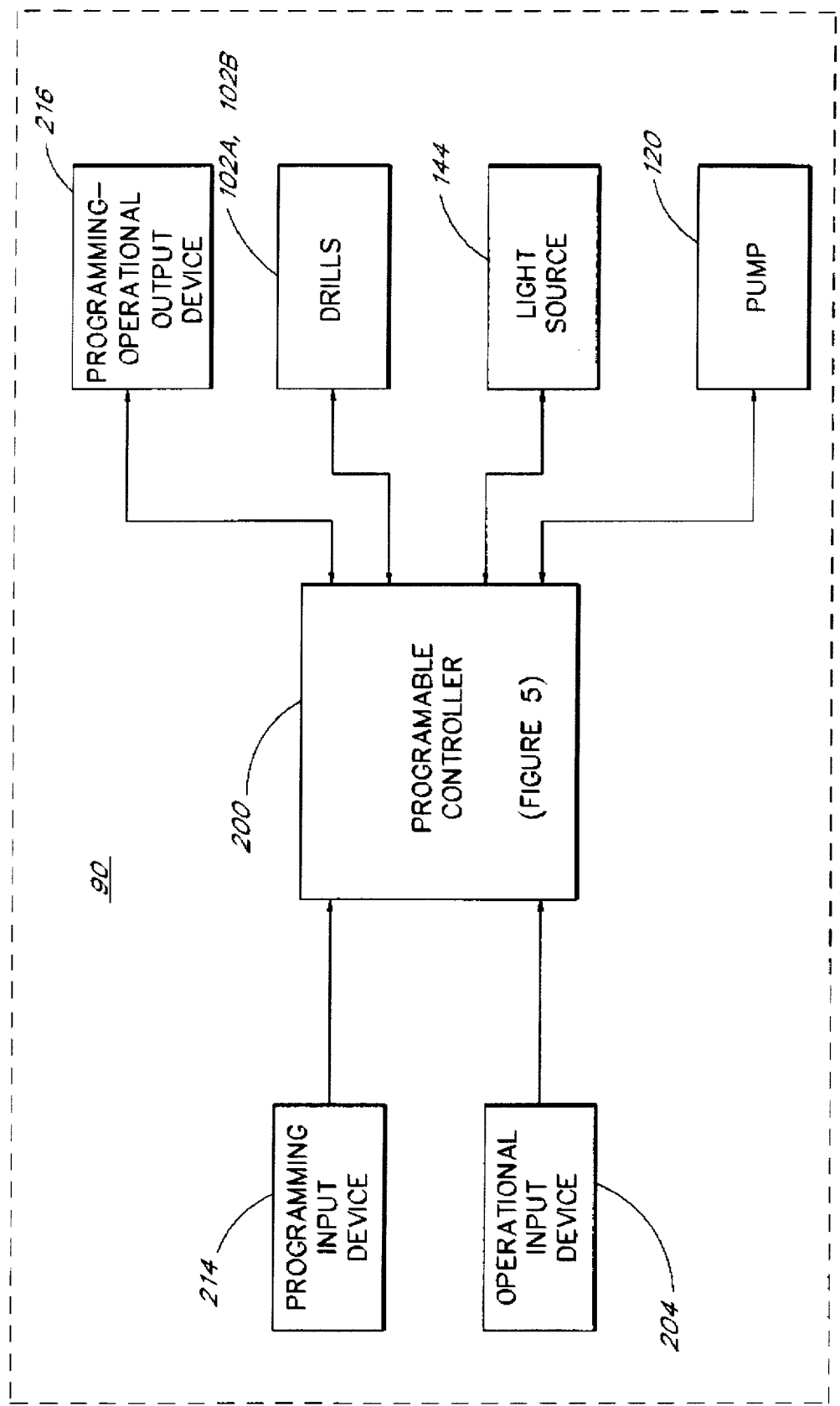
FIG. 4 illustrates a functional block diagram of the dental drilling system of FIG. 1.

FIG. 4 illustrates a functional block diagram of the drilling system 90 of FIG. 1. As described above, the drilling system 90 comprises the programmable controller 200, the drills 102A, 102B, the light source 144 and the pump 120, also shown in FIG. 1. The drilling system 90 additionally comprises a programming input device 214, a programming-operational output device 216, and an operational input device 204. The keypad 114 of FIG. 1 provides a programming input device 214 of FIG. 2. The LCD display 116 and the LED display 118 of FIG. 1 provide programming-operational output devices 216 of FIG. 2. The foot switch 104 of FIG. 1 provides an operational input device 204 of FIG. 2.

Figure 5:
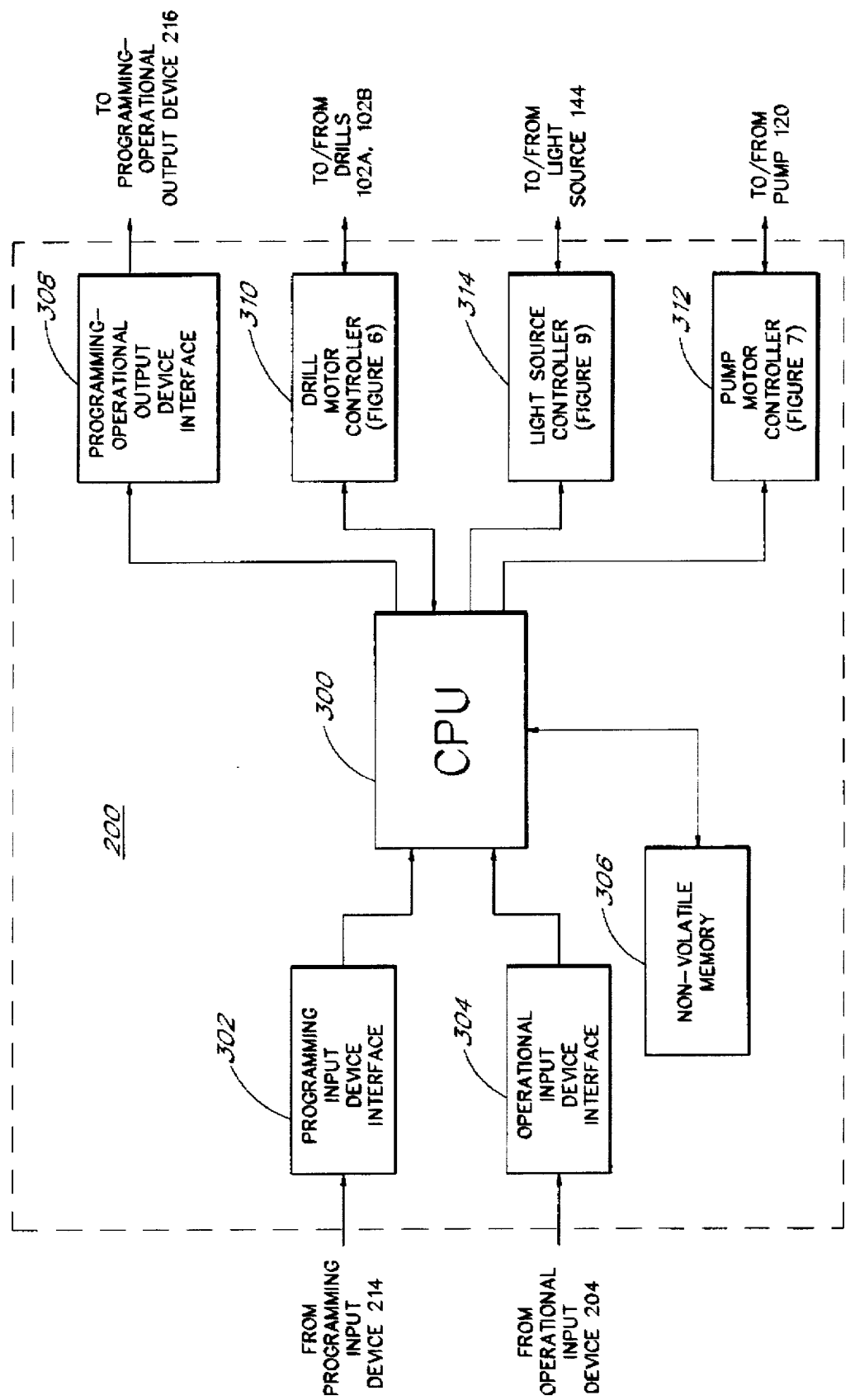
FIG. 5 illustrates a functional block diagram of the programmable controller of FIG. 4.

FIG. 5 illustrates a functional block diagram of the programmable controller 200 of FIGS. 1 and 4. The programmable controller 200 comprises a CPU 300, a programming input device interface 302, an operational input device interface 304, a nonvolatile memory 306, a programming-operational output device interface 308, a drill motor controller 310, a light source controller 314 and a pump motor controller 312.

Figure 6:
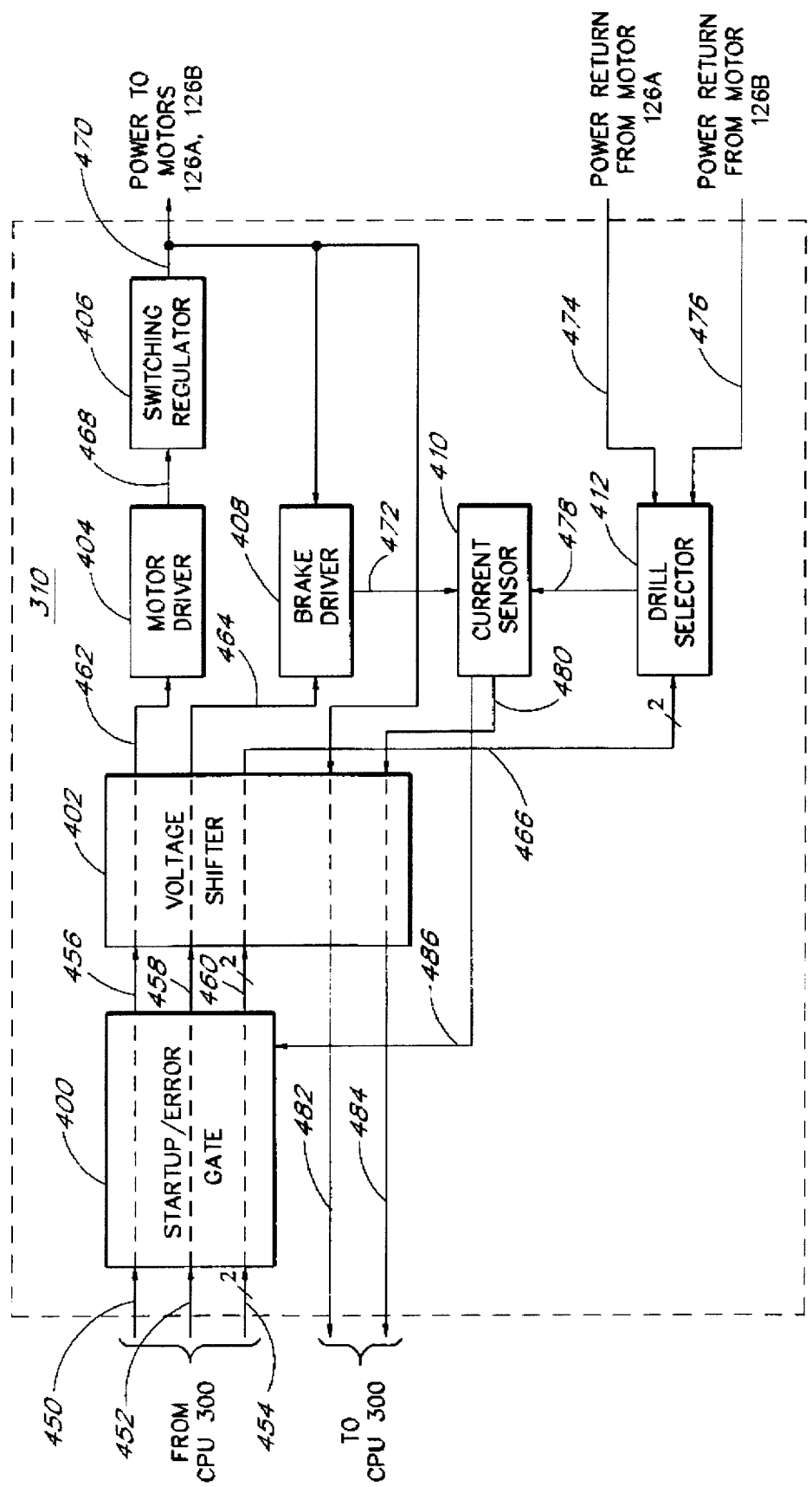
FIG. 6 illustrates a functional block diagram of the drill motor controller of FIG. 5.

FIG. 6 illustrates the drill motor controller 310 of FIG. 5. The drill motor controller 310 comprises a startup/error gate 400, a voltage shifter 402, a motor driver 404, a switching regulator 406, a brake driver 408, a current sensor 410, a drill selector 412, a set of four motor PWM lines 450, 456, 462 and 468, a set of three brake PWM lines 452, 458 and 464, a set of three pairs of drill selection lines 454,460 and 466, a motor power line 470, a set of four motor current lines 472,478,480 and 484, a set of two motor return lines 474 and 476, a motor voltage line 482 and an over-current error line 486.

Figure 7:
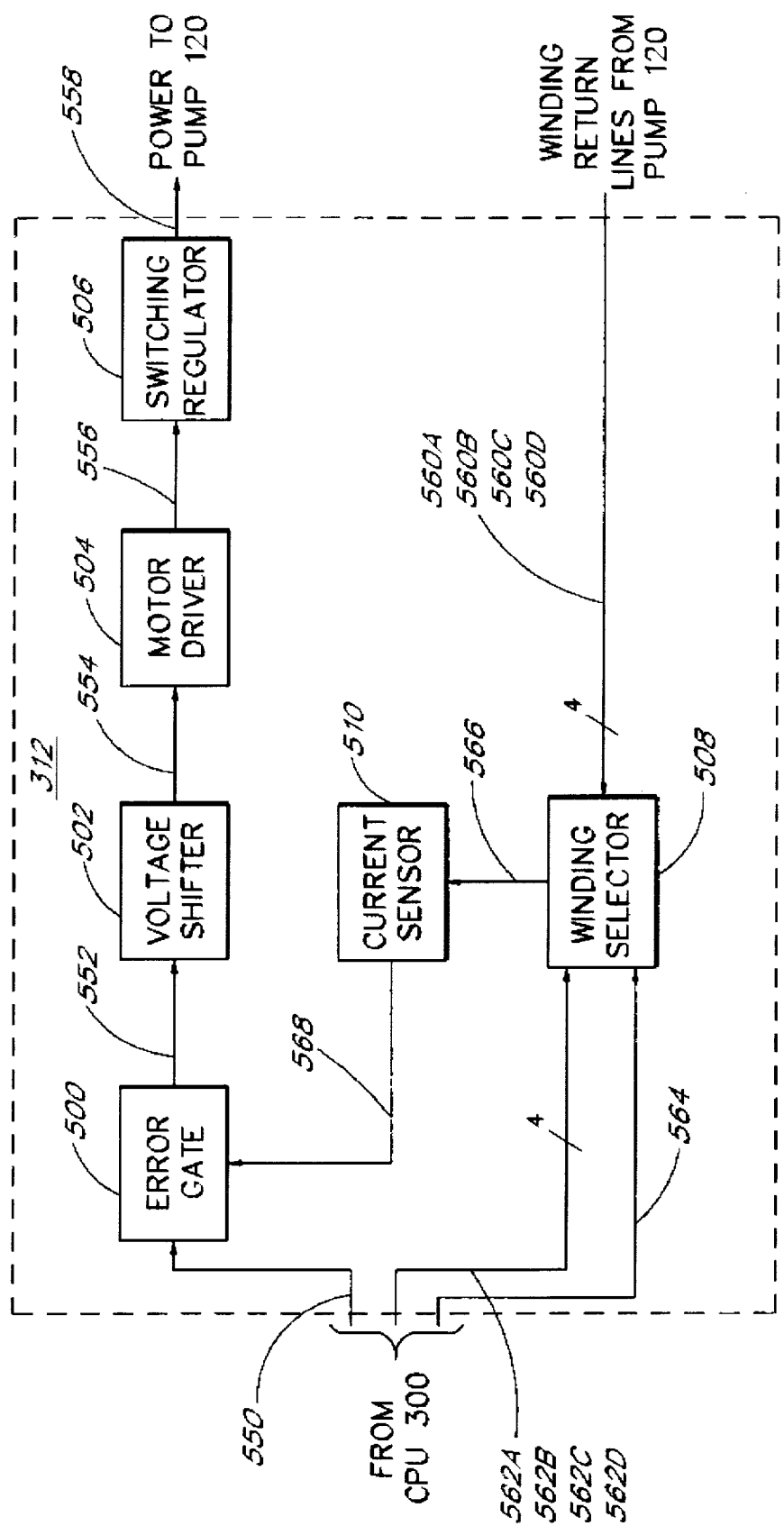
FIG. 7 illustrates a functional block diagram of the pump motor controller of FIG. 5.

FIG. 7 illustrates the pump motor controller 312 of FIG. 5. The pump motor controller 312 comprises an error gate 500, a voltage shifter 502, a motor driver 504, a switching regulator 506, a winding selector 508, a current sensor 510, a set of four motor PWM lines 550, 552, 554 and 556, a motor power line 558, a set of four winding return lines 560A, 560B, 560C and 560D, a set of four winding enable lines 562A, 562B, 562C and 562D, a motor enable line 564 and a set of two motor current lines 566 and 568.

Figure 8:
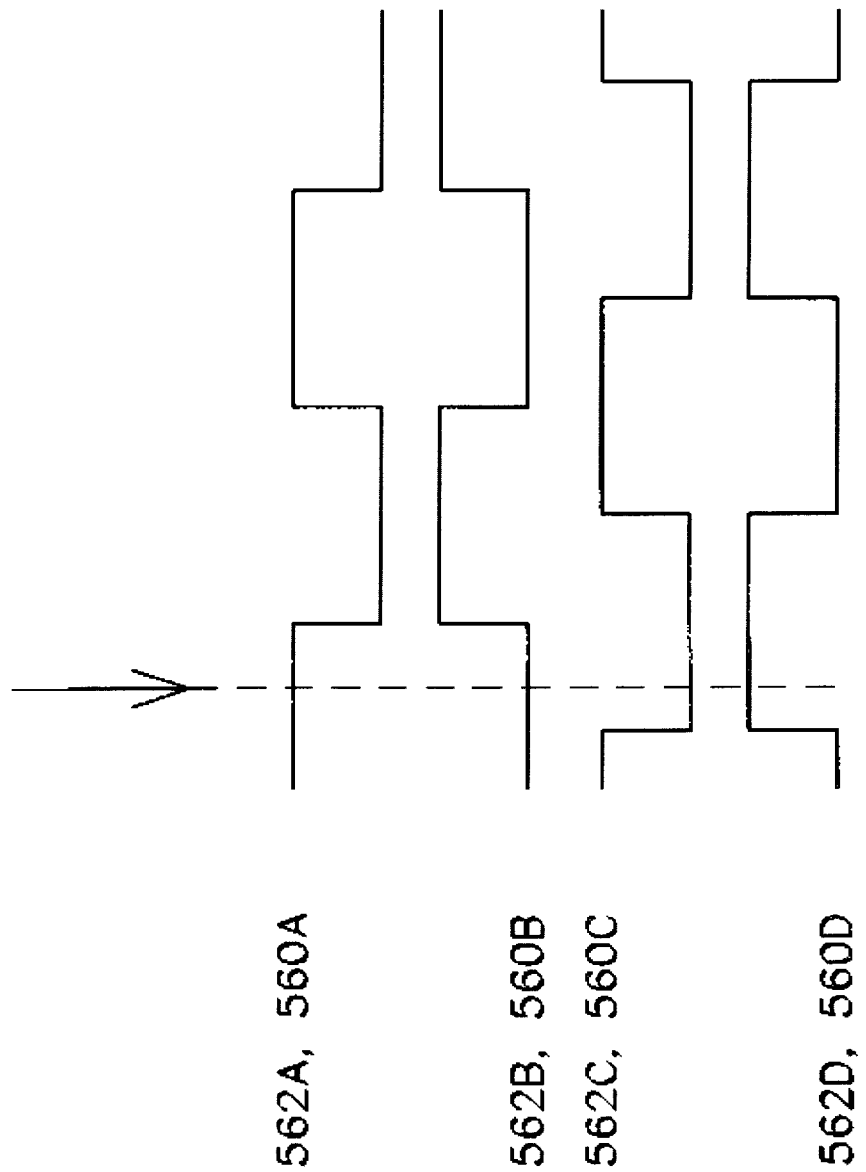
FIG. 8 illustrates a set of signals applied to the winding return lines of FIG. 7 to drive the pump motor.

FIG. 8 illustrates a set of four preferred signal wave forms that are applied to the winding enable lines 562A, 562B, 562C and 562D and the winding return lines 560A, 560B, 560C and 560D to activate the pump 120.

Figure 9:
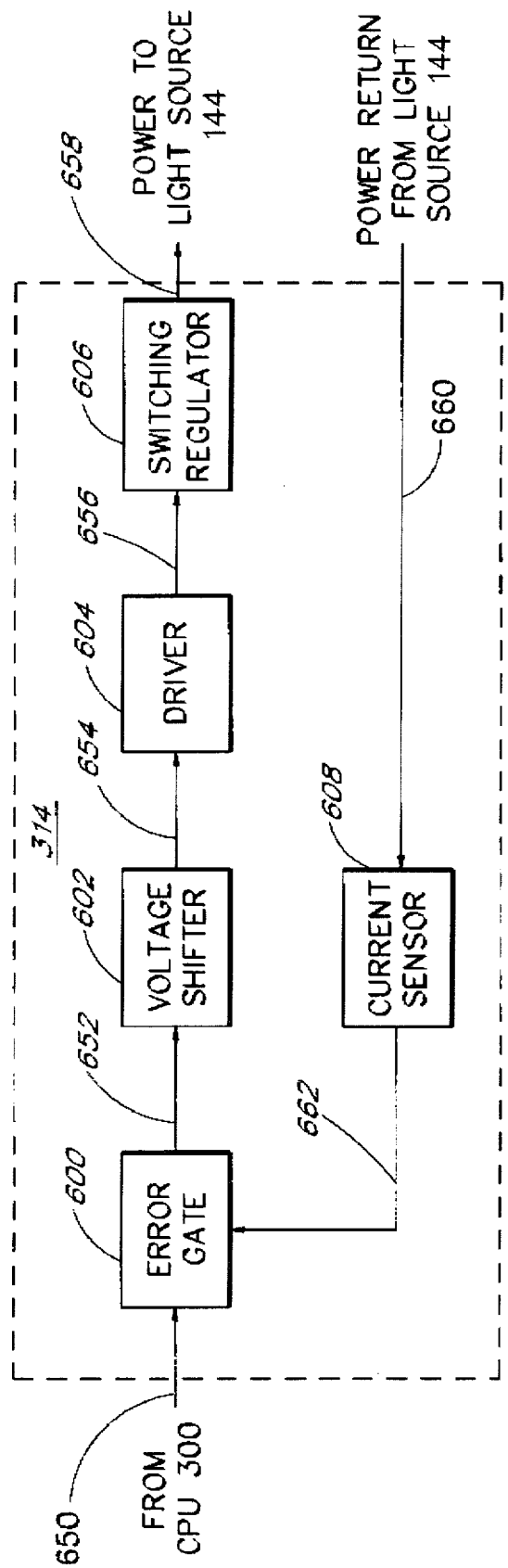
FIG. 9 illustrates a functional block diagram of the light source controller of FIG. 5.

FIG. 9 illustrates the light source controller 314 of FIG. 5. The light source controller 314 comprises an error gate 600, a voltage shifter 602, a driver 604, a switching regulator 606, a current sensor 608, a set of four light source PWM lines 650, 652, 654 and 656, a light source power line 658, a light source return line 660 and a light source current line 662.

Referring again to FIG. 1, the drill cable 106A is connected between the drill 102A and the drill cable connector 112A of the programmable control unit 100. The drill cable 106A comprises the motor power line 470 and the motor return line 474, shown in FIG. 6. The drill 102A has a motor 126A connected to the drill cable 106A. The shaft 128A is connected to the motor 126A. The handpiece 130A mounts over the shaft 128A. The gear train 132A engages with the shaft 128A. The drilling bit 150 is connected to the gear train 132A. Similarly, the drill cable 106B is connected between the drill 102B and the drill cable connector 112B of the programmable control unit 100. The drill cable 106B comprises the motor power line 470 and the motor return line 476, shown in FIG. 6. The drill 102B has a motor 126B connected to the drill cable 106B. The shaft 128B is connected to the motor 126B. The handpiece 130B mounts over the shaft 128B. The gear train 132B engages with the shaft 128B. The tapping bit 152 is connected to the gear train 132B.

The light source 144 is connected to the programmable control unit 100 by the light source cable 143. The light source cable 143 comprises the light source power line 658 and the light source return line 660, shown in FIG. 9. During an operation, the light source 144 is preferably attached to an outside surface of either the handpiece 130A or the handpiece 130B, whichever is currently in use, so that the light source 144 illuminates the area of the operation. The programmable control unit 100 is connected to the foot switch 104 by the foot switch cable 108. The on/off switch 136 of the foot switch 104 encompasses substantially all of an upper surface of the foot switch 104, except for the surface area occupied by the sequencer switch 138 and the reverse switch 140. The sequencer switch 138 is located near the left edge of the upper surface of the foot switch 104, and the reverse switch 140 is located near the right edge of the upper surface of the foot switch 104.

The pump 120 is attached to a side of the programmable control unit 100. The incoming fluid connector 124 provides a fluid communication between the pump 120 and an irrigation fluid reservoir (not shown). The outgoing fluid connector 110 provides a fluid communication from the pump 120 to an irrigation line (not shown) that is used to irrigate the area of the mouth on which the operation is being performed. The pump 120 is also connected to the programmable control unit 100 by an electrical pump cable (not shown). The pump cable (not shown) comprises the motor power line 558 and the set of four winding return lines 560A, 560B, 560C and 560D, shown in FIG. 7. The keypad 114, the LCD display 116, the LED display 118 and the drill cable connectors 112A and 112B are mounted on a front panel of the programmable control unit 100.

Referring to FIG. 4, the programming input device 214, the operational input device 204, the programming-operational output device 216, the drills 102A and 102B, the light source 144 and the pump 120 are all connected to the programmable controller 200. Within the programmable controller 200, as shown in FIG. 5, the programming input device interface 302, the operational input device interface 304, the nonvolatile memory 306, the programming-operational output device interface 308, the drill motor controller 310, the light source controller 314 and the pump motor controller 312 are connected to the CPU 300. The programming input device interface 302 is connected to the programming input device 214 of FIG. 4. The operational input device interface 304 is connected to the operational input device 204 of FIG. 4. The programming-operational output device interface 308 is connected to the programming-operational output device 216 of FIG. 4. The drill motor controller 310 is connected to the drills 102A, 102B of FIG. 4. The light source controller 314 is connected to the light source 144 of FIG. 4. The pump motor controller 312 is connected to the pump 120 of FIG. 4.

Within the drill motor controller 310, as shown in FIG. 6, the startup/error gate 400 is connected to the CPU 300 of FIG. 5 by the motor PWM line 450, the brake PWM line 452 and the pair of drill selection lines 454. The startup/error gate 400 is connected to the voltage shifter 402 by the motor PWM line 456, the brake PWM line 458 and the pair of drill selection lines 460. The voltage shifter 402 is connected to the motor driver 404 by the motor PWM line 462. The motor driver 404 is connected to the switching regulator 406 by the motor PWM line 468. The switching regulator 406 is connected to the motors 126A and 126B of the drills 102A and 102B of FIGS. 1 and 4 by the motor power line 470. The motor power line 470 is also connected to the brake driver 408 and to the voltage shifter 402. The voltage shifter 402 is connected to the brake driver 408 by the brake PWM line 464. The brake driver 408 is connected to the current sensor 410 by the motor current line 472. The current sensor 410 is connected to the voltage shifter 402 by the motor current line 480. The voltage shifter 402 is connected to the drill selector 412 by the pair of drill selection lines 466. The drill selector 412 is connected to the current sensor 410 by the motor current line 478. The drill selector 412 is connected to the motor 126A of the drill 102A, of FIGS. 1 and 4, by the motor return line 474, and to the motor 126B of the drill 102B, of FIGS. 1 and 4, by the motor return line 476. The voltage shifter 402 is connected to the CPU 300 of FIG. 5 by the motor voltage line 482 and the motor current line 484. Finally, the current sensor 410 is connected to the startup/error gate 400 by the over-current error line 486.

Within the pump motor controller 312, as shown in FIG. 7, the error gate 500 is connected to the CPU 300 of FIG. 5 by the motor PWM line 550. The error gate 500 is connected to the voltage shifter 502 by the motor PWM line 552. The voltage shifter 502 is connected to the motor driver 504 by the motor PWM line 554. The motor driver 504 is connected to the switching regulator 506 by the motor PWM line 556. The switching regulator 506 is connected to the pump 120 of FIGS. 1 and 4 by the motor power line 558. The current sensor 510 is connected to the error gate 500 by the motor current line 568. The winding selector 508 is connected to the current sensor 510 by the motor current line 566. The winding selector 508 is connected to the pump 120 of FIGS. 1 and 4 by the set of four winding return lines 560A, 560B, 60C and 560D. The winding selector 508 is connected to the CPU 300 of FIG. 5 by the motor enable line 564 and the set of four winding enable lines 562A, 562B, 562C and 562D.

Within the light source controller 314, as shown in FIG. 9, the error gate 600 is connected to the CPU 300 of FIG. 5 by the light source PWM line 650. The error gate 600 is connected to the voltage shifter 602 by the light source PWM line 652. The voltage shifter 602 is connected to the driver 604 by the light source PWM line 654. The driver 604 is connected to the switching regulator 606 by the light source PWM line 656. The switching regulator 606 is connected to the light source 144 of FIGS. 1 and 4 by the light source power line 658. The current sensor 608 is connected to the error gate 600 by the light source current line 662 and to the light source 144 of FIGS. 1 and 4 by the light source return line 660.

Referring again to FIG. 4, the programmable controller 200 provides power and control signals to the drills 102A and 102B, the light source 144 and the pump 120. The drills 102A and 102B, the light source 144 and the pump 120 constitute operating devices. The programmable controller 200 controls specific operating parameters of the operating devices. For example, the programmable controller 200 controls the rotation speed, the direction of rotation, and the torque of the drilling bit 150 of the drill 102A (shown in FIG. 1), the intensity of illumination of the light source 144 and the flow rate generated by the pump 120. The drills 102A and 102B are generally used for procedures in a dental operation, such as drilling and tapping. The light source 144 is used to illuminate the area of the mouth being worked on, and the pump 120 provides irrigation fluid to the work area. The programmable controller 200 determines the desired values for the operating parameters of the operating devices based on a previously entered sequence of programming steps and based on inputs from the operational input device 204.

A sequence of programming steps can be entered into the programmable controller 200 using the programming input device 214. An operator entering a program is provided with information related to the programming of the programmable controller 200 by the programming-operational output device 216. The keypad 114 of FIG. 1 constitutes a programming input device 214, while the LCD display 116 and the LED display 118 of FIG. 1 constitute programming-operational output devices 216. Thus, an operator can enter the program into the programmable controller 200 using the keypad 114, and the operator can verify the entry of the program using the LCD display 116 and the LED display 118. One of many alternative programming input devices 214 is an ordinary computer keyboard, while one of many alternative programming-operational output devices 216 is a video monitor. A method of entering a program into the programmable controller 200 using the keypad 114, the LCD display 116 and the LED display 118 of FIG. 1 is described in greater detail below with reference to FIG. 10.

The keypad 114 of FIG. 1 also constitutes an operational input device 204. In addition, the foot switch 104 of FIG. 1 constitutes an operational input device 204. Many other devices can also be used as operational input devices 204. Using the keypad 114 and the foot switch 104 of FIG. 1, an oral surgeon can step through a previously programmed sequence of steps in the programmable controller 200 to set specific operating parameters of the operating devices to predetermined values. In addition, the oral surgeon can use the keypad 114 and the foot switch 104 to manually adjust the operational parameters of the operating devices during an operation, as required. The LCD display 116 and the LED display 118 of FIG. 1 also provide information about the operational parameters of the operating devices when using the programmable controller 200 to step through previously programmed steps and during manual operation. For example, when using the drill 102A with a drilling bit 150, the LCD display 116 indicates the rotational speed of the drilling bit 150. A method of using the programmable controller 200 to step through a sequence of preprogrammed steps during an operation is described in greater detail below with reference to FIG. 11.

Referring to FIG. 5, in the preferred embodiment, the CPU 300 is an Intel N80C196KC microprocessor. This CPU 300 has numerous advantageous features, such as internal random access memory (RAM) and several pulse width modulation (PWM) generators. The CPU 300 executes program code stored in the nonvolatile memory 306. The code is preferably stored in erasable programmable read-only memory (EPROM). The code executed by the CPU 300 in the nonvolatile memory 306 constitutes one or more system level programs or routines that control the overall operation of the CPU 300.

These system level programs provide at least three different modes of operation, a run mode, a manual mode and a program mode. The program mode allows an operator to enter a number of desired values for each operational parameter to be controlled into the programmable controller 200. This collection of desired values is referred to as a user level program. The user level program is organized into a number of program steps, where each program step comprises one desired value for each operational parameter to be controlled. A user level program preferably comprises one program step corresponding to each step of a dental operation or procedure. The run mode allows an operator to sequence through and activate each of the program steps, one at a time. When a specific program step is active, the programmable control unit 100 controls the operational parameters of the drilling system 90 to correspond to the respective desired values in the program step. Thus, when performing an oral surgery procedure, a surgeon can simply sequence through the program steps containing preprogrammed desired values and the programmable control unit 100 controls the operating parameters of the drilling system 90, as required. The manual mode allows an operator to manually adjust the values for the operational parameters and then activate the drilling system 90 to operate at the selected values. This feature is particularly useful when a surgeon wants a value for an operational parameter that is different from a preprogrammed value. A run mode program is described in greater detail below with reference to FIGS. 13A and 13B. A manual mode program is described in greater detail below with reference to FIG. 14. A program mode program is described in greater detail below with reference to FIGS. 15A, 15B, 15C, 15D and 15E.

Figure 10:
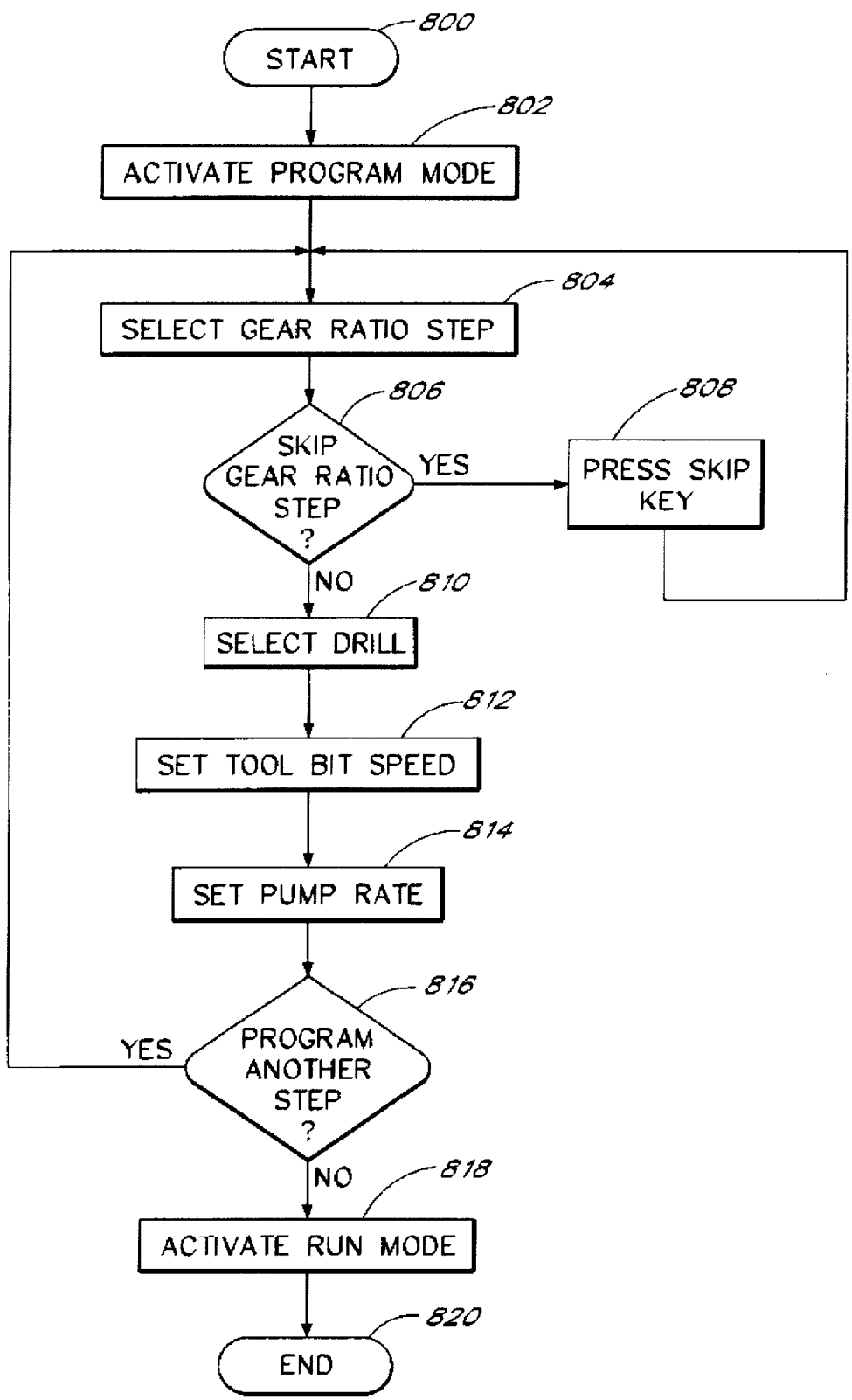
FIG. 10 is a flowchart illustrating a method for programming operating parameters into the programmable control unit of FIG. 1.

The program mode program allows the CPU 300 to receive an operator entered, user level program, according to the method of FIG. 10. During this method, the CPU 300 receives input data from the programming input device interface 302, which receives input data from the programming input device 214. This input data includes the desired values for the operating parameters to be controlled by the CPU 300. The CPU 300 generates data to indicate the status of the programming method and transmits this data to the programming-operational output device interface 308, which relays the data to the programming-operational output device 216. The user level program data received by the CPU 300 is stored in a section of the nonvolatile memory 306 that is programmable or writable by the CPU 300. This section of the nonvolatile memory 306 comprises electrically erasable programmable read-only memory (EEPROM) in the preferred embodiment. Other memory technologies may also be used to form the components of the nonvolatile memory 306, such as read-only memory (ROM) for the system level programs or a magnetic disk drive for either the system level programs or the user level program. Also, the nonvolatile memory 306 may store multiple user level programs simultaneously.

The CPU 300 receives operational input data from the operational input device interface 304, which receives the operational input data from the operational input device 204. The operational input data comprises, for example, a signal from the foot switch 104, shown in FIG. 1, indicating that the CPU 300 should reverse the direction of rotation of the drill bit 150. As another example, the operational input data may comprise signals from the keypad 114, shown in FIG. 1, indicating that an operating parameter should be incremented or decremented while the programmable control unit 100 is in the manual mode of operation. In the preferred embodiment, the programming-operational output device 216 is driven through the programming-operational output device interface 308 by the CPU 300 to provide information during the run mode and the manual mode, in addition to the program mode. For example, during an operation, the programming-operational output device 216 can be controlled to reflect the actual level of controlled operational parameters.

The CPU 300 generates control signals to the drill motor controller 310 for controlling the drills 102A and 102B; to the light source controller 314 for controlling the light source 144; and to the pump motor controller 312 for controlling the pump 120. The CPU 300 generates these control signals based on a previously entered user level program and current operational input data. The CPU 300 also receives signals from the drill motor controller 310 indicating the voltage applied to or generated by the active motor 126A or 126B and the current drawn or generated by the active motor 126A or 126B. The CPU 300 generates the control signals to the drill motor controller 310 in response to this feedback data from the motor controller 310.

Referring to FIG. 6, the CPU 300 provides signals to the drill motor controller 310 on the motor PWM line 450, the brake PWM line 452 and the pair of drill selection lines 454. The motor PWM line 450 and the brake PWM line 452 each carry a 0 to 5-volt pulse-width-modulation (PWM) signal, while the drill selection lines 454 carry 0 to 5-volt logic signals. The signal on the motor PWM line 450 is used to generate a drive voltage for driving the motors 126A and 126B of the drills 102A and 102B. The motors 126A and 126B comprise DC motors in the preferred embodiment. The drill motor controller 310 preferably generates a 0 to −45-volt DC signal to drive the motors 126A and 126B. The duty cycle of the PWM signal on the motor PWM line 450 determines the percentage of the full −45-volt DC signal that is applied to the motor 126A or 126B. For example, if the signal on the motor PWM line 450 has a 60% duty cycle, the motor 126A or 126B is driven by a −27 volt DC signal. Similarly, the PWM signal on the brake PWM line 452 controls the percentage of resistance applied by the brake driver 408 across the motor 126A or 126B to slow down the rotation of the motor 126A or 126B. The maximum resistance applied by the brake driver 408 may be 20 kilo ohms, for example. In this example, a signal with a 40% duty cycle on the brake PWM line 452 represents a braking resistance of 8 kilo ohms. The logic signals on the drill selection lines 454 indicate which of the drills 102A or 102B has been selected for operation, if any. Only one drill 102A or 102B can be active at a time in the present embodiment.

The startup/error gate 400 normally passes the signals on the motor PWM line 450, the brake PWM line 452 and the drill selection lines 454 through to the motor PWM line 456, the brake PWM line 458 and the drill selection lines 460, respectively. However, under specific circumstances, the startup/error gate 400 disables the PWM signals on the motor PWM line 456 and the brake PWM line 458, and the logic signals on the drill selection lines 460. For example, these signals are disabled when the programmable control unit 100 has initially been powered up or on a system reset. This condition continues until the CPU 300 has reached a predetermined location in a system level program that is executed after power up or reset. The disabling of these signals on system startup prevents the drill motor controller 10 from driving either motor 126A or 126B before the system has been initialized. In addition, the startup/error gate 00 disables these signals when an error condition has been detected. For example, if the motor 126A or 126B is drawing excessive current, the startup/error gate 400 disables the signals to shut off the motor 126A or 126B.

The voltage shifter 402 receives the signals on the motor PWM line 456, the brake PWM line 458 and the drill selection lines 460 from the startup/error gate 400. These signals are 0 to 5-volt signals. The voltage shifter 402 generates a 0 to 24-volt PWM signal on the motor PWM line 462 corresponding to the 0 to 5-volt PWM signal on the motor PWM line 456. The motor driver 404 generates a PWM signal with increased current on the motor PWM line 468 corresponding to the 0 to 24-volt PWM signal on the motor PWM line 462. The signal on the motor PWM line 468 has sufficient current to drive the motor 126A or 126B. The switching regulator 406 generates a 0 to −45-volt DC signal corresponding to the PWM signal on the motor PWM line 468. Thus, if the PWM signal on the motor PWM line 468 has a duty cycle of 90%, the switching regulator 406 generates a DC voltage that is 90% of −45 volts, or −40.5 volts. The switching regulator 406 applies this voltage to the motor power line 470 to provide a drive voltage to the motor 126A or 126B.

A switching regulator 406 is used with a PWM control signal on the motor PWM line 468, instead of a linear regulator and a linear control signal, to conserve energy and to reduce the amount of heat generated by the regulator. A linear regulator always generates a full voltage signal at the operating current. For example, in the present system, a linear regulator would generate a −45 volt signal. Then, if less than full voltage is required at the motor power line 470, the linear regulator would dissipate the excess voltage, resulting in increased power consumption and increased heat generation at the regulator. Thus, to obtain a drive voltage of −20 volts at the motor power line 470, a linear regulator would dissipate a power corresponding to −25 volts and the amount of current drawn by the motor 126A or 126B. In contrast, for almost all drive voltages at the motor power line 470, most of the power generated by the switching regulator 406 is transferred to the motor 126A or 126B.

The voltage shifter 402 also receives the drive voltage provided to the motor 126A or 126B on the motor power line 470. Based on this drive voltage on the motor power line 470, the voltage shifter 402 generates a PWM signal on the brake PWM line 464 corresponding to the 0 to 5-volt PWM signal on the brake PWM line 458. The PWM signal on the brake PWM line 464 varies between +5 volts and the motor drive voltage. Thus, when the signal on the brake PWM line 458 is at 0 volts, the signal on the brake PWM line 464 is +5 volts. When the signal on the brake PWM line 458 is at +5 volts, the signal on the brake PWM line 464 is at the drive voltage on the motor power line 470. The voltage shifter 402 also generates signals on the drill selection lines 466 corresponding to the signals on the drill selection lines 460. These signals on the drill selection lines 466 also vary between +5 volts and the motor drive voltage.

The brake driver 408 also receives the drive voltage on the motor power line 470. The brake driver 408 applies, for example, between 0 and 20 kilo ohms of resistance between the drive voltage on the motor power line 470 and a system ground connection. As described above, the resistance applied by the brake driver 408 is determined by the duty cycle of the PWM signal on the break PWM line 464. Applying a load across the drive voltage on the motor power line 470 drains rotational energy from the motor 126A or 126B to slow the motor 126A or 126B. When the brake driver 408 is actively slowing the motor 126A or 126B, the brake driver 408 provides a signal on the motor current line 472 representing the amount of current flowing through the motor 126A or 126B.

The drill selector 412 receives the signals from the drill selection lines 466 that indicate which, if any, of the motors 126A or 126B is active. If the motor 126A is active, the drill selector 412 effectively connects the motor return line 474 to ground to provide a power return for the motor 126A. Current then flows from the motor power line 470, through the motor 126A, to the motor return line 474 and to ground, thus driving the motor 126A with the drive voltage on the motor power line 470. If the drill 102B is selected, the drill selector 412 effectively connects the motor return line 476 to ground, providing a return path for current from the motor 126B. This allows the drive voltage on the motor power line 470 to power the motor 126B. The drill selector 412 generates a signal on the motor current line 478 indicating the amount of current flowing through the selected motor 126A or 126B. The current sensor 410 receives a signal on the motor current line 472 indicating the current level at the brake driver 408 and a signal on the motor current line 478 indicating the current level at the drill selector 412. The current sensor 410 generates a signal on the motor current line 480 indicating the appropriate current level. In the preferred embodiment, the motor 126A or 126B is not driven by the motor driver 404 and slowed by the brake driver 408 simultaneously. Thus, either the signal on the motor PWM line 462 or the signal on the brake PWM line 464 is inactive at any given time. Depending on whether the motor driver 404 or the brake driver 408 is active at a specific time, the current sensor 410 determines the appropriate current level from either the motor current line 478 or the motor current line 472, respectively.

The voltage shifter 402 receives the current level signal on the motor current line 480 and generates a corresponding 0 to 5-volt signal on the motor current line 484. Also, the voltage shifter 402 receives the 0 to −45-volt DC signal on the motor power line 470 and generates a corresponding 0 to 5-volt signal on the motor voltage line 482. The motor voltage line 482 and the motor current line 484 are connected to an analog-to-digital converter on the CPU 300. By receiving the signals on the motor voltage line 482 and the motor current line 484, the CPU 300 can determine the actual voltage and current applied to or generated by the motor 126A or 126B.

The CPU 300 uses these values to compute the torque applied to the tool bit 150, 152, 154 or 156 and the rotational speed of the tool bit 150, 152, 154 or 156, based on the characteristics of the motor 126A or 126B and of the gear train 132A or 132B. Except for the DC resistance of the motor 126A or 126B, the torque applied to the tool bit 150, 152, 154 or 156 is almost a linear function of the current drawn by the motor 126A or 126B and of the gear ratio of the gear train 132A or 132B, while the rotational speed is almost a linear function of the voltage applied to the motor 126A or 126B and of the gear ratio of the gear train 132A or 132B. Sufficiently precise transfer functions for the torque and rotational speed of particular motors 126A or 126B and gear trains 132A or 132B can be obtained from manufacturer data sheets or by analytical methods. The CPU 300 uses the results of these computations to determine appropriate duty cycles for the PWM signals on the motor PWM line 450 and on the brake PWM line 452. By adjusting the duty cycles of the PWM signals, the CPU 300 can limit the torque and the speed produced by the motor 126A or 126B, to meet user specifications.

Referring again to FIG. 7, the CPU 300 generates a 0 to 5-volt PWM signal on the motor PWM line 550. The duty cycle of the PWM signal on the motor PWM line 550 represents the percentage of full voltage to be applied to the pump 120. The drive voltage for the pump 120 varies vary between 0 and −24 volts DC. Thus, a duty cycle of 75% on the motor PWM line 550 represents a drive voltage of −18 volts. The error gate 500 normally passes the signal on the motor PWM line 550 through to the motor PWM line 552. However, in the event of an error, the error gate 500 disables the signal on the motor PWM line 552. An error condition can arise under various circumstances, such as, for example, when the pump 120 draws a current that is greater than a predetermined maximum value. The voltage shifter 502 takes the 0 to 5-volt PWM signal on the motor PWM line 552 and generates a corresponding 0 to 24-volt PWM signal on the motor PWM line 554. The motor driver 504 generates a signal on the motor PWM line 556 corresponding to the signal on the motor PWM line 554. The signal on the motor PWM line 556, however, has sufficient current capability to drive the pump 120. The switching regulator 506 converts the PWM signal on the motor PWM line 556 into a DC drive voltage to the pump 120. As described above, the drive voltage ranges from 0 to −24 volts DC. The drive voltage is applied to the motor power line 558 to drive the motor of the pump 120. Again, a switching regulator 506 is used with a PWM control signal on the motor PWM line 556, instead of a linear regulator and a linear control signal, to conserve energy and to reduce heat generation.

The pump 120 comprises a four-phase stepper motor in the preferred embodiment. The windings of the stepper motor of the pump 120 are connected to the winding return lines 560A, 560S, 560C and 560D. The winding return lines 560A, 560S, 560C and 560D are also connected to the winding selector 508. As is well-known to a person of skill in the art, a stepper motor is driven by applying a different sequence of pulses to each of the winding connectors of the stepper motor. For example, if the signals illustrated in FIG. 8 are applied to the winding return lines 560A, 560B, 560C and 560D, respectively, with a drive voltage applied to the motor power line 558, the pump 120 is activated to pump fluid through the outgoing fluid connector 110. An irrigation hose (not shown) transfers the fluid from the outgoing fluid connector 110 to the site of the operation.

The CPU 300 generates signals having the waveform illustrated in FIG. 8 and applies these signals to the winding enable lines 562A, 562B, 562C and 562D. The CPU 300 also generates a pump enable signal on the motor enable line 564. The winding selector 508 receives the signals on the motor enable line 564 and on the winding enable lines 562A, 562B, 562C and 562D. If the signal on the motor enable line 564 is active, the winding selector 508 applies the signals on the winding enable lines 562A, 562B, 562C and 562D to the winding return lines 560A, 560B, 560C and 560D, respectively. The power supplied at the motor power line 558 propagates through the appropriate windings and to the winding return lines 560A, 560B, 560C and 560D that are at an active low level. For example, at a point in time indicated by an arrow in FIG. 8, power from the motor power line 558 propagates through the windings of the pump 120 that are connected to the winding return lines 560B and 560C. The drive voltage applied to the motor power line 558 and the frequency of the square wave signals applied to the winding return lines 560A, 560B, 560C and 560D, as illustrated in FIG. 8, determine the fluid flow rate generated by the pump 120.

The winding selector 508 provides a signal on the motor current line 566 indicating the amount of current drawn by the pump 120. The current sensor 510 determines whether this current consumption by the pump 120 exceeds a predefined maximum level. An over-current signal is provided to the error gate 500 by the current sensor 510 on the motor current line 568.

Referring to FIG. 9, the CPU 300 generates a 0 to 5-volt PWM signal on the light source PWM line 650. The duty cycle of the PWM signal on the light source PWM line 650 determines the percentage of full voltage that is applied to the light source 144. The drive voltage varies between 0 and 24 volts DC. In the preferred embodiment, the drive voltage is typically between 6 and 6.3 volts. Thus, the PWM signal on the light source PWM line 650 typically has a duty cycle of approximately 25%. However, in the preferred embodiment, when initially illuminating the light source 144, the duty cycle of the PWM signal on the light source PWM line 650 gradually increases from 0 to approximately 25% to provide a soft start for the light source 144. This gradual increase in the drive voltage for the light source 144 extends the useful life of conventional light sources, such as incandescent bulbs, by eliminating the stress on the filament caused by sudden increases in the drive voltage.

Normally the error gate 600 applies the PWM signal from the light source PWM line 650 to the light source PWM line 652. However, under error conditions, such as where the light source 144 draws an excessive current level, the error gate 600 disables the PWM signal on the light source PWM line 652. The voltage shifter 602 receives a 0 to 5-volt PWM signal on the light source PWM line 652 and generates a corresponding 0 to 24-volt PWM signal on the light source PWM line 654. The driver 604 generates a signal on the light source PWM line 656 that corresponds to the PWM signal on the light source PWM line 654. The signal generated by the driver 604 has sufficient current capacity to drive the light source 144. The switching regulator 606 converts the PWM signal on the light source PWM line 656 into a DC voltage for driving the light source 144. The switching regulator 606 places this drive voltage on the light source power line 658. Again, a switching regulator 606 is used with a PWM control signal on the light source PWM line 656, instead of a linear regulator and a linear control signal, to conserve energy and to reduce heat generation.

The return line from the light source 144 is connected to the light source return line 660, which is connected to the current sensor 608. The current sensor 608 determines the current flowing through the light source 144. The current sensor 608 generates a signal on the light source current line 662, indicating whether the current drawn by the light source 144 exceeds a predetermined maximum value. The error gate 600 receives the signal on the light source current line 662 to determine whether there is an overcurrent condition.

As described above, the nonvolatile memory 306 of FIG. 5 comprises EEPROM for storing user level programming data related to operational parameters of operating devices. In the preferred embodiment, the programming data is stored in the form of a table in memory. Each column in the table contains all of the desired values for a single operating parameter; while each row in the table contains data representing a single desired value for every operating parameter to be controlled by the programmable control unit 100. For example, each row may have data values corresponding to which drill 102A or 102B is selected for operation, the rotational speed of the tool bit 150,152,154 or 156, the torque applied to the tool bit 150, 152, 154 or 156, the flow rate generated by the pump 120 and the illumination status of the light source 144 (e.g. on or off). In one embodiment, each row of the programming table is associated with a specific fixed gear ratio of the gear train 132A or 132B. For example, a first row may be associated with a gear ratio of 3:1. Thus, each row of the table is a "gear ratio step". Also, there is preferably at least one gear ratio step associated with each of the possible gear ratios of the gear train 132A or 132B for a particular implementation. In one embodiment of the present invention, one row of the table is dedicated to storing information related to desired values for the operating parameters when the drill 102A or 102B is operated in a reverse direction. In this embodiment, this reverse step could be altered in a manner similar to the modification of normal gear ratio steps, but would typically only be accessed during run mode when the reverse switch 140 on the foot switch 104 has been activated.

Again as described above, the nonvolatile memory 306 also comprises an EPROM that stores system level programs that are executed by the CPU 300 of FIG. 5. One of these system level programs, the program mode program, provides the capability to enter a program into the programmable control unit 100 to specify a number of desired values for the operating parameters. Different desired values correspond to different steps of a dental operation. Essentially, this program mode program allows an operator to move among the different locations of the above-described programming table and change the stored values, as desired. The program mode program comprises a number of C programming language Case statements, or similar programming functions. The different elements of the Case statements correspond to the different keys on the keypad 114. The function executed upon activation of each of the keys on the keypad 114 varies, depending on the location of execution within the program mode program. Basically, the up-arrow key 142E and the down-arrow key 142H allow the operator either to move to a different row in the programming table or to change the value in the current table location, such as by incrementing or decrementing the current value. The left-arrow key 142G and the right-arrow key 142I allow the operator to move to different columns within a row. The program mode program is described in greater detail below with reference to FIGS. 15A, 15B, 15C, 15D and 15E.

FIG. 10 is a flow chart illustrating a method for programming the programmable control unit 100 of FIG. 1. The method begins at a block 800. At a process block 802, an operator activates the program mode of the programmable control unit 100 by pressing the program-mode key 142B. The programmable control unit 100 has three modes of operation. The program mode allows an operator to enter desired values for operational parameters. The run mode allows a surgeon to step through a preprogrammed set of operational parameter values. The manual mode allows a surgeon to manually adjust the operational parameters to desired values. The CPU 300 of FIG. 5 responds to the activation of the program-mode key 142B by beginning execution of the above-described program mode program. The program mode program copies the above-described program table from the nonvolatile memory 306 to internal RAM for modification during execution of the program mode program. The program mode program then displays, on the LCD display 116 and the LED display 118, the gear ratio and the presently stored values for each of the operating parameters associated with the current gear ratio step.

At a process block 804, the operator selects a gear ratio step for editing. As indicated above, the operator uses the up-arrow key 142E and the down-arrow key 142H to move to different rows in the programming table. The operator can only move to different rows in the table if there is no cursor appearing in the LCD display 116. If a cursor does appear on the LCD display 116, the operator can press the right-arrow key 142I or the left-arrow key 142G until the cursor disappears. As the operator moves to different gear ratio steps, the program mode program displays the corresponding gear ratio and operating parameter values.

When the LCD display 116 displays the gear ratio step that the operator wants to modify, the operator advances to a decision block 806. At the decision block 806, the operator determines whether the current gear ratio step should be skipped. If the step is skipped, a surgeon will not have access to that step during run mode. If the current gear ratio step should be skipped, the operator advances to a process block 808. Otherwise, the operator advances to a process block 810. At the process block 808, the operator presses the skip key 142D. The program mode program responds by writing a value into the table indicating that the current gear ratio step should be skipped. The operator returns to the process block 804.

At the process block 810, the operator moves the cursor to a drill selection indicator on the LCD display 116 using the right-arrow key 142I or the left-arrow key 142G. Next, the operator selects the desired drill 102A or 102B by pressing the up-arrow key 142E or the down-arrow key 142H until the desired drill 102A or 102B is indicated. At a process block 812, the operator selects both a desired rotational speed and a desired torque setting for the tool bit 150, 152, 154 or 156 in a similar manner. A desired rotational speed and a desired torque setting can both be maintained simultaneously. Specifically, the operator moves the cursor to the drill speed indicator on the LCD display 116 using the right-arrow key 142I or the left-arrow key 142G. Next, the operator presses the up-arrow key 142E to increment the displayed bit speed, or the down-arrow key 142H to decrement the displayed bit speed. Next, the operator moves the cursor to the drill torque indicator on the LCD display 116 using the right-arrow key 142I or the left-arrow key 142G. Next, the operator presses the up-arrow key 142E to increment the displayed torque setting, or the down-arrow key 142H to decrement the displayed torque setting. At a process block 814, the operator selects a desired irrigation fluid flow rate generated by the pump 120 in a similar manner.

At a decision block 816, the operator determines whether another gear ratio step should be programmed. If another step should be programmed, the operator returns to the process block 804. Otherwise, the operator advances to a process block 818. At the process block 818, the operator presses the run-mode key 142A. In response, the input data program updates the EEPROM in the nonvolatile memory 306 with any changes that have been made during the current execution of the program mode program. Next, the CPU 300 terminates execution of the program mode program and begins execution of the run mode program. The programmable control unit 100 now enters the run mode, allowing a surgeon to step through the preprogrammed steps. The method of FIG. 10 ends at a block 820.

During the run mode, a surgeon presses the sequencer key 138 of the foot switch 104 to step through the preprogrammed gear ratio steps. At each gear ratio step, the programmable control unit 100 controls the operational parameters of the operating devices to achieve the previously selected values. However, the drill 102A or 102B and the pump 120 are not activated until the surgeon activates the on/off switch 136 of the foot switch 104.

Figure 11A:
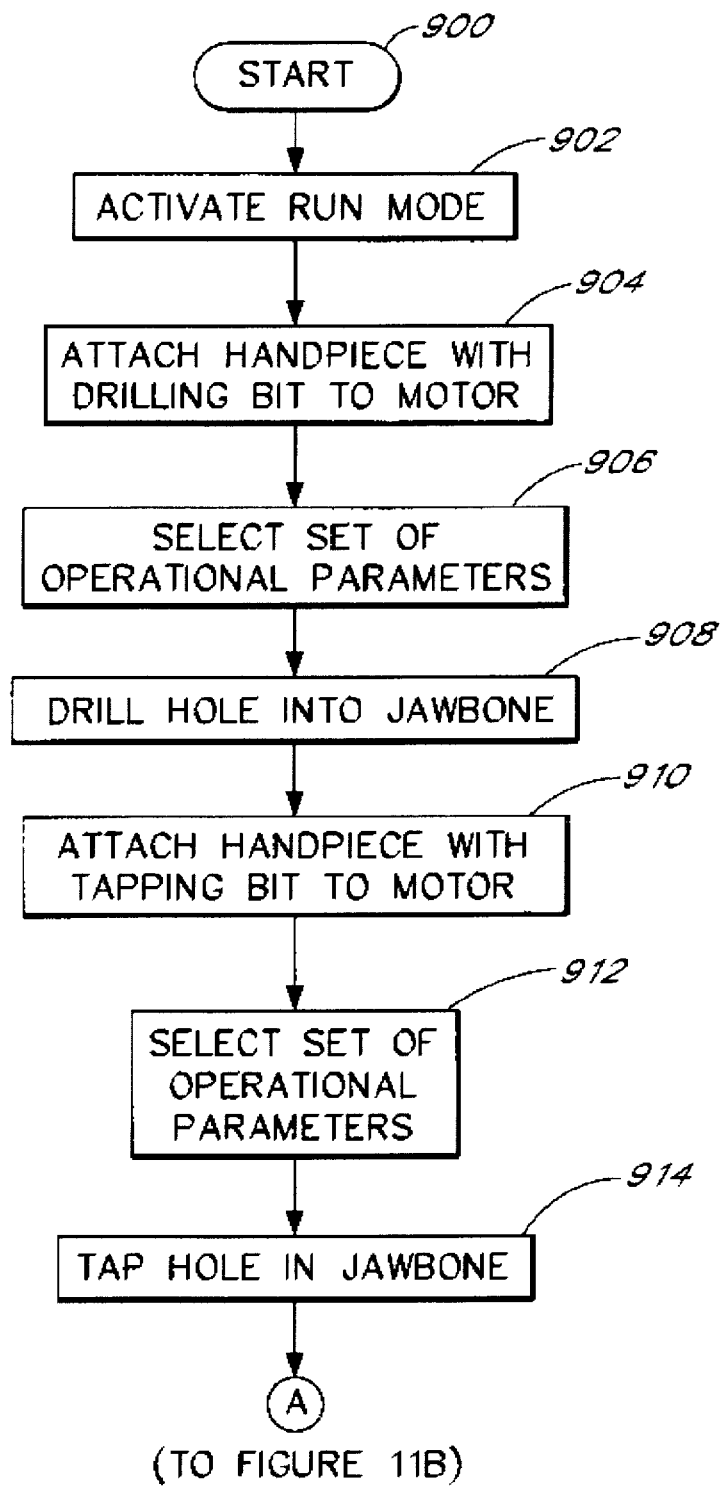
FIGS. 11A and 11B form a flowchart illustrating a method for using the dental drilling system of FIG. 1 to perform a sequence of steps in a dental implant procedure.
Figure 11B:
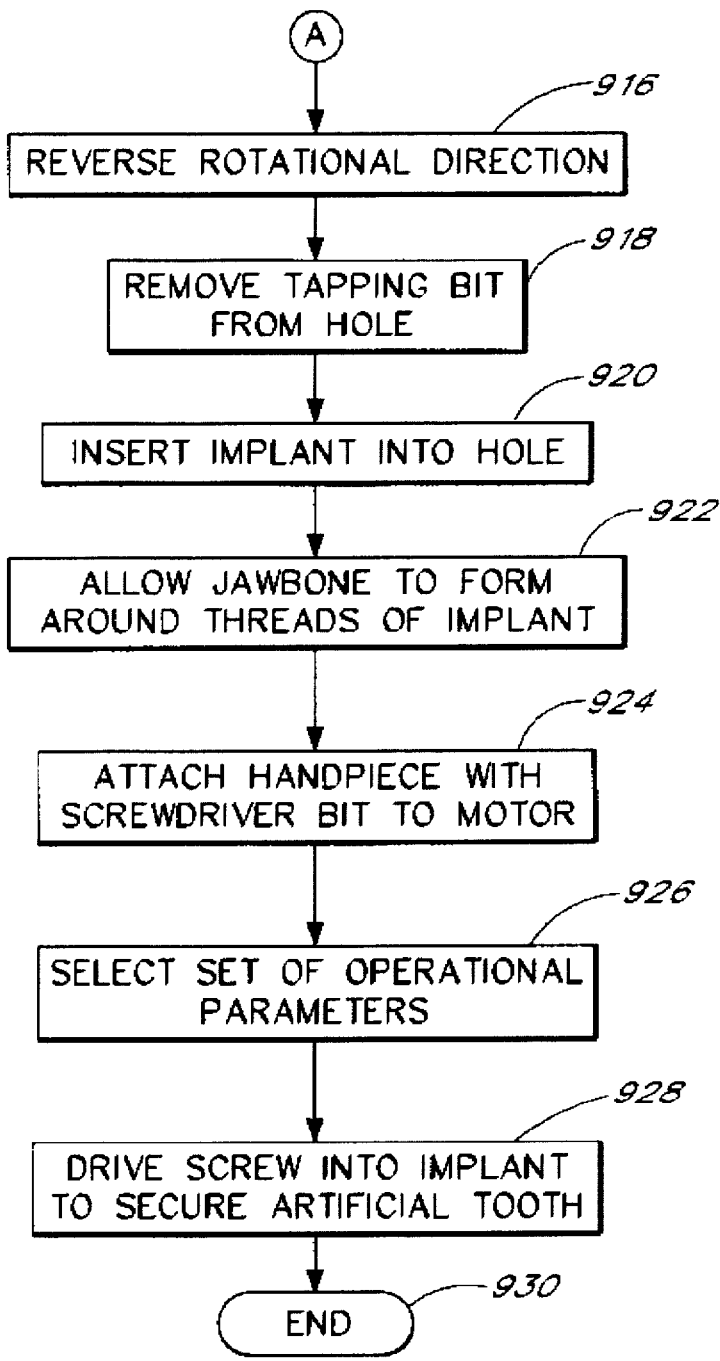
Figure 12:
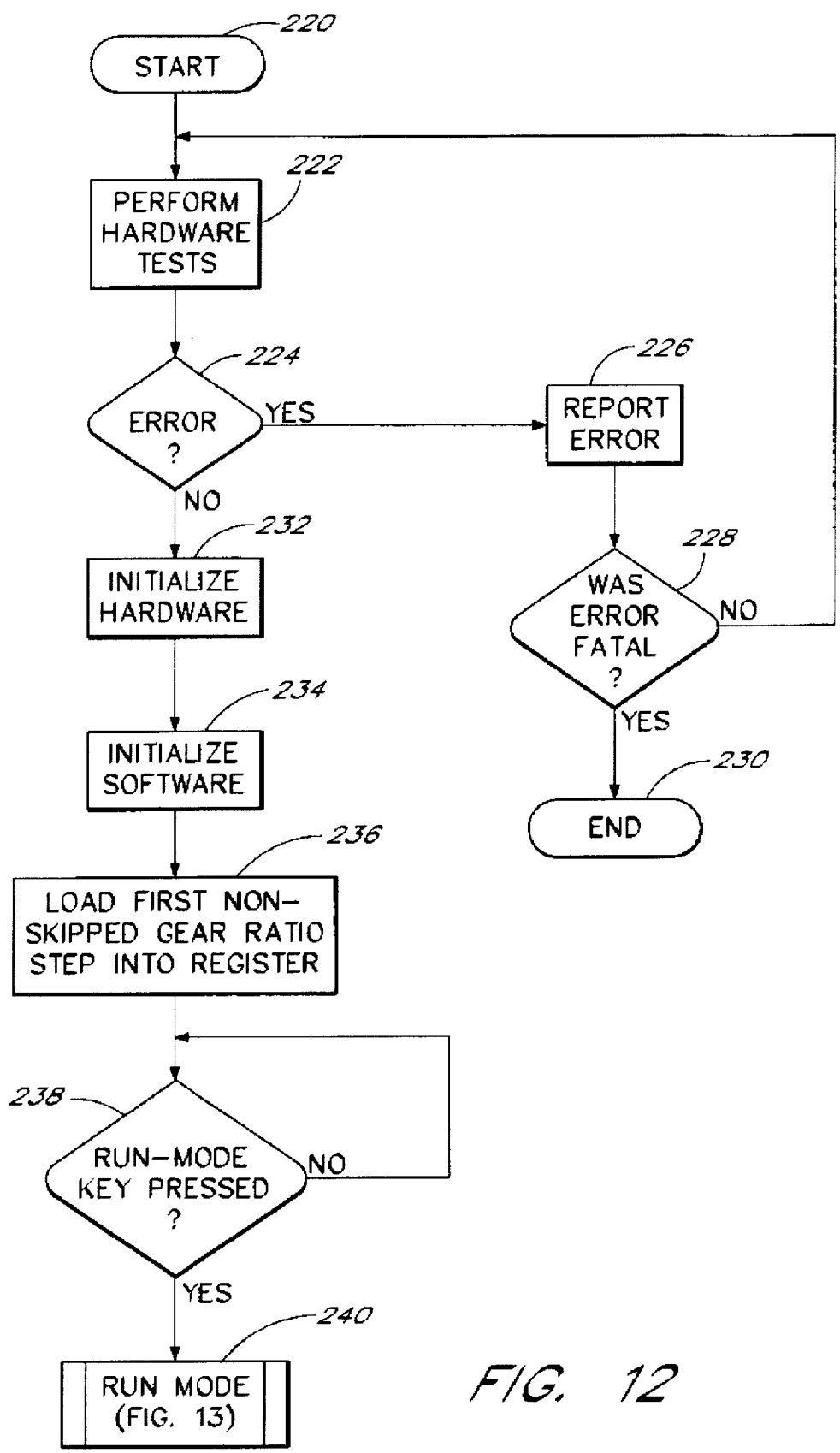
FIG. 12 is a flowchart of a system level initialization routine executed by a CPU of the programmable controller of FIG. 5.

FIGS. 11A and 11B form a flow chart illustrating a method for performing an exemplary dental implant operation using the dental drilling system 90. The dental implant operation of this example involves a single artificial tooth mounted to a single tooth fixture, and a single implant. The method begins at a block 900, shown in FIG. 11A. At a process block 902, the surgeon or an assistant places the programmable control unit 100 into the run mode, if the run mode is not already active, by pressing the run-mode key 142A. The CPU 300 responds to this action by beginning execution of the run mode program. The run mode program indicates the current set of preprogrammed values for the operational parameters on the LCD display 116 and the LED display 118. The run mode program is described in greater detail below with reference to FIGS. 13A and 13B.

At a process block 904, the surgeon attaches a handpiece 130A or 130B, with a drilling bit 150, to one of the motors 126A or 126B. The handpiece 130A or 130B must have a gear train 132A or 132B with an appropriate gear ratio for drilling a hole into the jawbone of the patient, using the drilling bit 150. At a process block 906, the surgeon activates the sequencer switch 138 of the foot switch 104 to step through the gear ratio steps to find the gear ratio step that has the correct gear ratio and the desired values for the operational parameters. For drilling a hole into the jawbone of the patient, a specific rotational speed for the drilling bit 150 is selected. The torque setting is typically set at a relatively high value, but low enough to ensure that the drilling bit 150 is not damaged by excessive torque. Preferably, each combination of gear ratio and set of operational parameters required for the current operation has already been programmed into the programmable control unit using the method of FIG. 10. When the correct gear ratio step is displayed on the LCD display 116 and the LED display 118, the surgeon advances to a process block 908.

At the process block 908, the surgeon presses the on/off switch 136 of the foot switch 104 to activate the selected drill 102A or 102B. The drill 102A or 102B selected to be active in the entered user level program must correspond with the drill 102A or 102B that has the drilling bit 150. When the surgeon presses the on/off switch 136, the programmable control unit 100 activates the drill 102A or 102B, the pump 120 and the light source 144 to operate at the previously entered values. The surgeon now drills a hole into the jawbone of the patient using the drilling bit 150. The programmable control unit 100 controls the motor 126A or 126B to drive the drilling bit 150 at the preselected rotational speed, while also monitoring the torque generated by the motor 126A or 126B to ensure that the maximum torque setting is not exceeded.

At a process block 910, the surgeon attaches a handpiece 130A or 130B, having a tapping bit 152, to one of the motors 126A or 126B. The gear train 132A or 132B of the handpiece 130A or 130B must have a gear ratio that is appropriate for tapping the hole in the jawbone of the patient, using the tapping bit 152. Again, the motor 126A or 126B selected must correspond to the previously entered program. At a process block 912, the surgeon again activates the sequencer switch 138 of the foot switch 104 to step through the gear ratio steps to find the gear ratio step that has the correct gear ratio and the desired values for the operational parameters. For tapping the hole, a specific torque setting is selected that prevents the tapping bit 152 from stripping the newly formed threads when the tapping bit 152 bottoms out. When the correct gear ratio step is displayed on the LCD display 116 and the LED display 118, the surgeon advances to a process block 914.

At the process block 914, the surgeon presses the on/off switch 136 of the foot switch 104 to activate the selected drill 102A or 102B. When the surgeon presses the on/off switch 136, the programmable control unit 100 activates the drill 102A or 102B, the pump 120 and the light source 144 to operate at the previously entered values. The surgeon now taps the hole that had been drilled in the process block 908, using the tapping bit 152. The programmable control unit 100 controls the motor 126A or 126B to drive the tapping bit 152 at the preselected torque, while simultaneously monitoring the rotational speed generated by the motor 126A or 126B. The torque control feature of the present invention is described in greater detail below with reference to a process block 928.

At a process block 916, shown in FIG. 11B, the surgeon presses the reverse switch 140 on the foot switch 104 to reverse the direction of rotation of the tapping bit 152. This enables the surgeon to remove the tapping bit 152 from the hole at a process block 918, without damaging the newly formed threads in the jawbone. At this point the patient's jawbone has a threaded hole, where the threads are actually formed out of the material of the jawbone.

At a process block 920, the surgeon screws an implant into the hole in the patient's jawbone. The implant has a threaded male end for mating with the threaded hole in the jawbone, just like an ordinary screw. The implant also has a threaded hole opposite the threaded male end, for receiving an ordinary screw. At a process block 922, the surgeon waits for the jawbone to grow back around the threads of the male end of the implant to secure the implant into the jawbone. If the formation of the jawbone around the implant causes the implant to move to an undesirable angle with respect to the jawbone, the surgeon may use an abutment between the implant and the artificial tooth fixture to compensate for the movement of the implant. To simplify the present example, an abutment is not used.

During a subsequent appointment, typically with a dentist that is not an oral surgeon, the dentist advances to a process block 924. At the process block 924, the dentist attaches a handpiece 130A or 130B having an appropriate gear ratio and either a slotted screw driving bit 154 or a hex screw driving bit 156 to the motor 126A or 126B. The screw driving bit 154 or 156 is used to drive a screw through the artificial tooth fixture and into the implant. The screw driving bit 154 or 156 selected depends on the type of screw used. At a process block 926, the dentist selects the appropriate gear ratio step in the same manner as described above with reference to the process blocks 906 and 912.

At the process block 928, the dentist drives the screw through the artificial tooth fixture and into the implant. The dentist places a mounting surface of the tooth fixture against a mounting surface of the implant so that a hole in the mounting surface of the tooth fixture generally aligns with a hole in the implant. Next, the dentist places the screw through the hole in the tooth fixture until the screw makes contact with the threads of the threaded hole of the implant. The dentist places the tip of the screw driving bit 154 or 156 against a head end of the screw, and engages the screw driving bit 154 or 156 with a slot or a hexagon-shaped hole in the head end of the screw. The dentist activates the drill 102A or 102B by pressing the on/off switch 136 of the foot switch 104. When the screw driving bit 154 or 156 causes the screw to rotate, the threads of the screw engage with the threads of the implant and the screw is driven into the implant. When the screw is driven completely into the implant, so that the head end of the screw presses the mounting surface of the tooth fixture against the mounting surface of the implant, the screw stops progressing into the implant.

At this point, if the screw continues to rotate, one or more of three possible situations could arise. First, the threads of the screw could damage, or strip, the threads of the implant. Second, the threads of the implant could strip the threads of the screw. And third, the rotational movement could be transferred to the dental implant, causing the dental implant to tear loose from the jawbone and begin to rotate. However, for this step of the operation, a maximum torque is programmed into the corresponding gear ratio step that does not allow any of these situations to arise. The torque is set at a high enough level to drive the screw into the implant with sufficient force so that the screw is not likely to loosen up and cause the artificial tooth to become loose. On the other hand, the torque is set at a low enough level so that, when a force prevents the screw from proceeding into the implant, the drill motor 126A or 126B stalls instead of damaging the threads of the screw or the implant, and instead of tearing the implant loose from the jawbone. A recommended torque is typically specified by the manufacturer of a dental implant set.

Using the torque control feature of the present invention, a dentist can simply drive the screw into the implant until the motor 126A or 126B stalls and the screw is automatically driven to the desired torque. After driving the screw into the implant to secure the artificial tooth fixture, the dentist covers the heads of the screws with a filler. The method of FIG. 11 ends at a block 930.

Although the invention has been described in connection with oral surgery, the invention could also be used in other types of surgery, such as maxillofacial reconstructive surgery, podiatry, plastic surgery, orthopedic surgery, including arthroscopy, and endodontic procedures. Also, although the invention has been described in connection with steps of drilling, tapping and inserting screws and implants, the invention could also be used for sawing (sagittal, reciprocating and oscillating), filing, reaming and dermabradding.

FIGS. 12, 13A, 13B, 14, 15A, 15B, 15C, 15D, 15E, 16A, 16B, and 16C are flowcharts illustrating system-level programs that are executed by the CPU 300 of FIG. 5. When the programmable control unit 200 is powered up, the CPU 300 begins execution at a block 220 of FIG. 12. At a process block 222, the CPU 300 performs a set of hardware diagnostic tests. These diagnostic tests verify that numerous aspects of the electronic circuitry of the programmable control unit 200 are operating correctly. For example, one diagnostic test verifies that the CPU 300 can communicate with the nonvolatile memory 306 of FIG. 5. The diagnostic tests also verify some aspects of the dental drilling system 90 that are exterior to the programmable control unit 200. For example, one diagnostic test verifies that either the drill 102A is connected to the drill cable connector 112A or the drill 102B is connected to the drill cable connector 112B.

At a decision block 224, the CPU 300 determines whether the diagnostic tests that were performed during the process block 222 resulted in an error. If there was an error, the CPU 300 advances to a process block 226. Otherwise, the CPU 300 advances to a process block 232. At the process block 226, the CPU 300 indicates the type of error that has occurred on either the LCD display 116 or the LED display 118. At a decision block 228, the CPU 300 determines whether the error is a fatal error. An error is characterized as fatal if the programmable control unit 200 is shut down without allowing an operator to correct the erroneous condition. One example of a fatal error is if the CPU 300 cannot communicate with the nonvolatile memory 306. An example of a nonfatal error is where there is no drill 102A or 102B connected to either of the drill cable connectors 112A or 112B. If the error is fatal, the CPU 300 advances to a block 230 and terminates execution of the program. The programmable control unit 200 is disabled until power to the unit is cycled. If the error is not fatal, the CPU 300 returns to the process block 222. The CPU 300 continues executing the hardware diagnostic tests of the process block 222 until the erroneous condition has been corrected.

As described above, when the hardware diagnostic tests of the process block 222 are executed without detecting an error condition, the CPU 300 advances to the process block 232. At the process block 232, the CPU 300 initializes the hardware of the programmable control unit 200. The hardware initialization comprises a number of steps, such as initializing timers and registers within the CPU 300. At a process block 234, the CPU 300 initializes the software routines that are executed by the CPU 300. For example, the CPU 300 initializes variables that are used by the different system level programs that are run on the CPU 300. At this point the CPU 300 also detects whether the EEPROM portion of the nonvolatile memory 306 has been previously programmed. If the EEPROM has not been programmed, the CPU 300 indicates this condition in either the LCD display 116 or the LED display 118. If the EEPROM has been programmed, the CPU 300 reads the above-described programming table from the EEPROM to internal RAM. If the EEPROM has not been programmed, the CPU 300 establishes a programming table in internal RAM using default values. After the initial loading of the programming table from EEPROM into RAM, the programming table in RAM is used, except for the writing of the programming table into EEPROM after executing the program mode program, as described below with reference to FIGS. 15A, 15B, 15C, 15D and 15E.

At a process block 236, the CPU 300 checks a set of skip variables corresponding to each of the gear ratio steps in the programming table. Each skip variable indicates whether the corresponding gear ratio-step should be skipped when operating in the run mode. The CPU 300 loads the data from the first nonskipped gear ratio step into a parameter control register. The parameter control register provides a set of desired values for the different operating parameters to be controlled by the programmable control unit 100. The contents of the parameter control register are utilized to control the operating parameters when the drilling system 90 is activated by pressing the on/off switch 136 of the foot switch 104 during the run mode or the manual mode. At a decision block 238, the CPU 300 determines whether the run mode key 142A has been pressed. If the run mode key 142A has not been pressed, the CPU 300 continues to execute the decision loop 238. If the run mode key 142A has been pressed, the CPU 300 advances to a process block 240. At the process block 240, the CPU 300 begins execution of the run mode program. The operation of the run mode program is described in greater detail below with reference to FIGS. 13A and 13B.

Figure 13A:
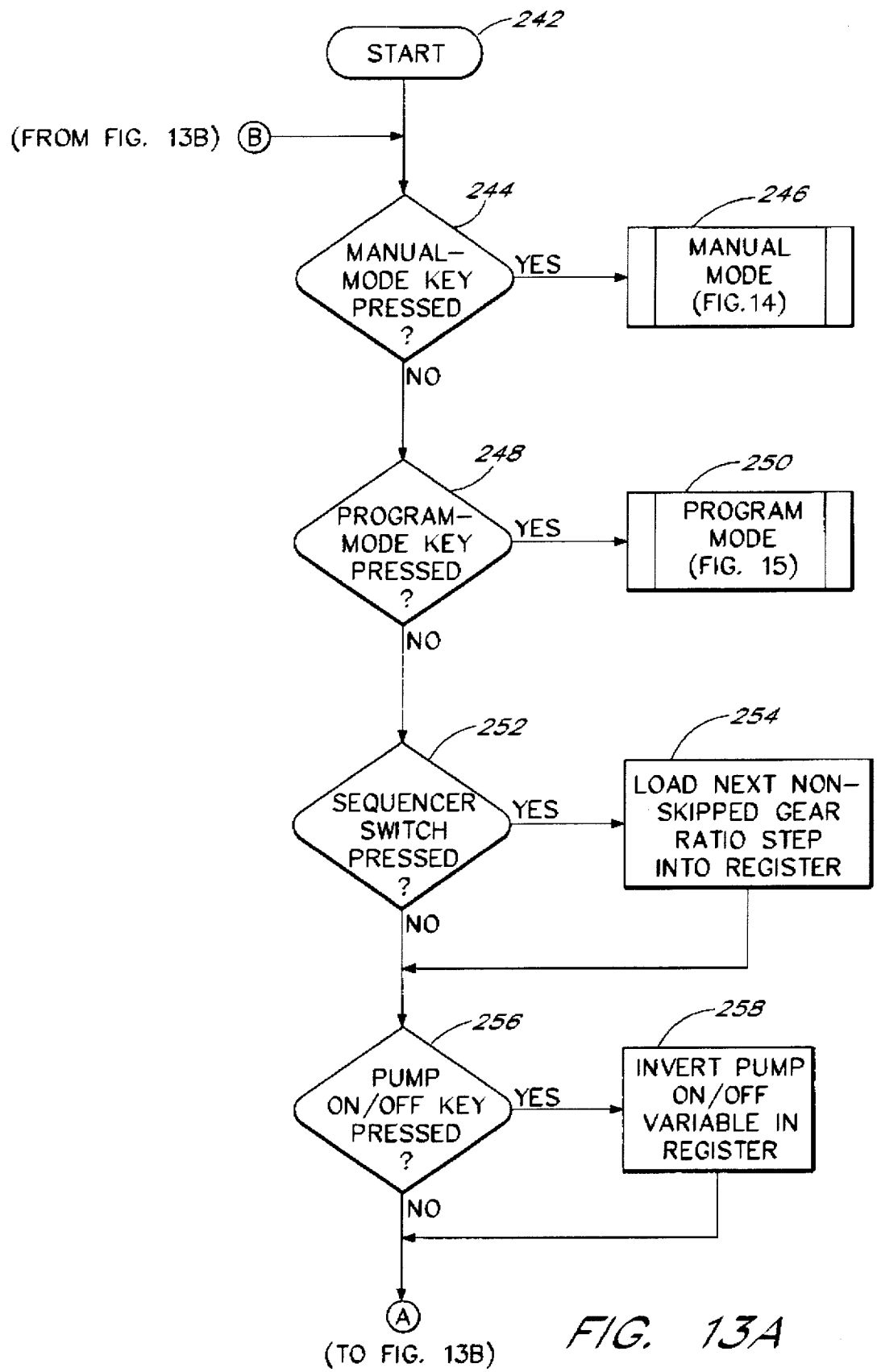
FIGS. 13A and 13B form a flowchart of a system level run mode program executed by a CPU of the programmable controller of FIG. 5.
Figure 13B:
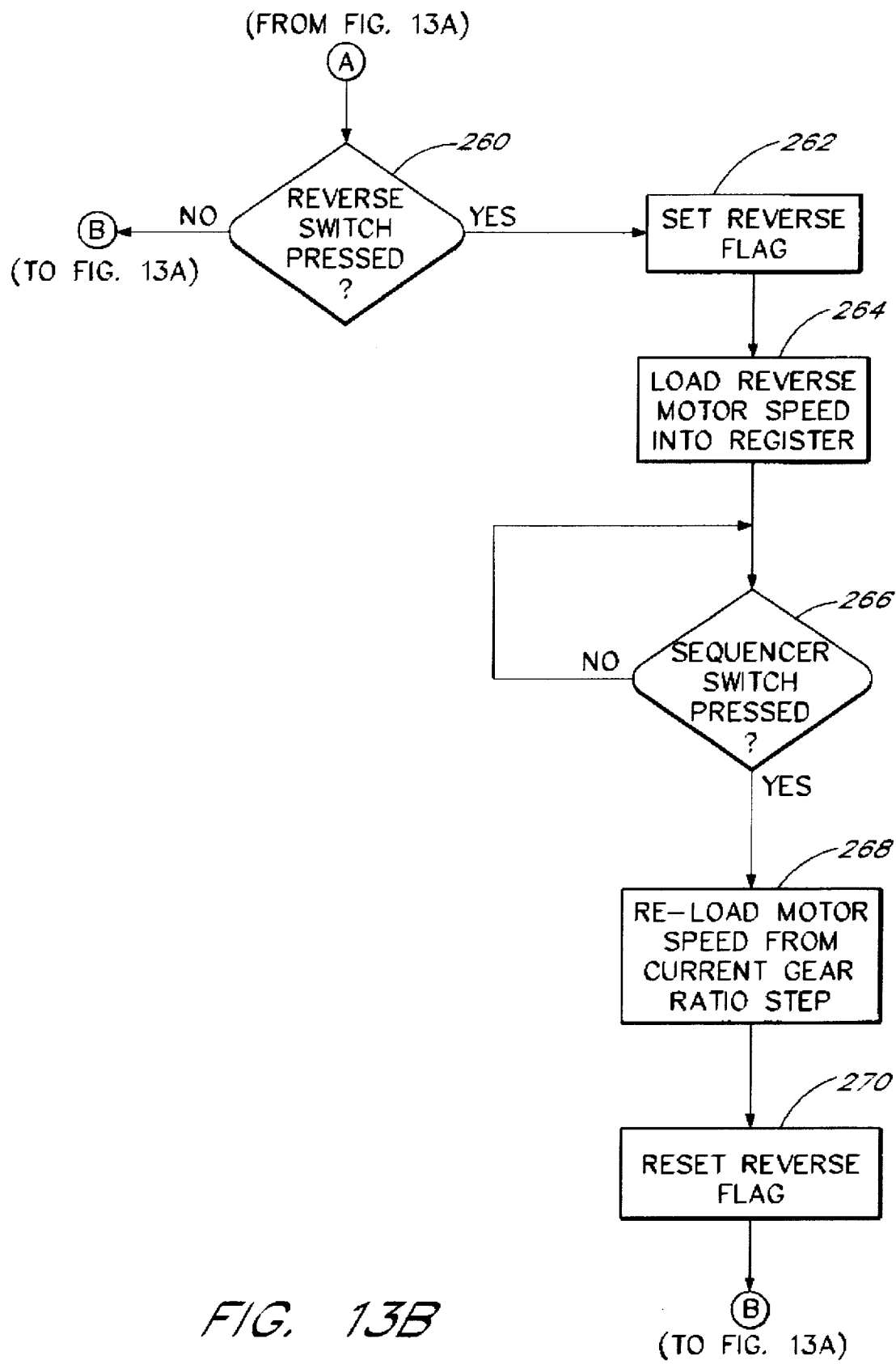

Referring to FIG. 13A, the run mode program begins at a block 242. At a decision block 244, the CPU 300 determines whether the manual mode key 142C has been pressed. If the manual mode key 142C has been pressed, the CPU 300 advances to a process block 246. Otherwise, the CPU 300 advances to a decision block 248. At the process block 246, the CPU 300 terminates execution of the run mode program and begins to execute the manual mode program. The manual mode program is described in greater detail below with reference to FIG. 14.

At the decision block 248, the CPU 300 determines whether the program-mode key 142B has been pressed. If the program mode key 142B has been pressed, the CPU 300 advances to a process block 250. Otherwise, the CPU 300 advances to a decision block 252. At the process block 250, the CPU 300 terminates execution of the run mode program and begins to execute the program mode program. The program mode program is described in greater detail below with reference to FIGS. 15A, 155, 15C, 15D and 15E. After beginning the run mode program at the process block 240 of FIG. 12, the CPU 300 continuously executes the run mode program, the manual mode program, or the program mode program until the execution is halted either by a fatal error that prevents further execution or by turning power off to the programmable control unit 200.

At the decision block 252, the CPU 300 determines whether the sequencer switch 138 of the foot switch 104 has been pressed. If the sequencer switch 138 has been pressed, the CPU 300 advances to a process block 254. Otherwise, the CPU 300 advances to a decision block 256. At the process block 254, the CPU 300 loads the data from the next nonskipped gear ratio step of the programming table into the parameter control register. After the process block 254, the CPU 300 continues to the decision block 256.

At the decision block 256, the CPU 300 determines whether the pump on/off key 142F has been pressed. If the pump on/off key 142F has been pressed, the CPU 300 advances to a process block 258. Otherwise, the CPU 300 advances to a decision block 260 of FIG. 135. At the process block 258, the CPU 300 inverts a pump on/off variable in the parameter control register. The pump on/off variable in the parameter control register controls whether the pump 120 is driven to generate an irrigation fluid flow. After the process block 258, the CPU 300 advances to the decision block 260 of FIG. 135.

At the decision block 260, the CPU 300 determines whether the reverse switch 140 of the foot switch 104 has been pressed. If the reverse switch 140 has not been pressed, the CPU 300 returns to the decision block 244 of FIG. 13A.

If the reverse switch 140 has been pressed, the CPU 300 advances to a process block 262.

At the process block 262, the CPU 300 sets a reverse flag that is internal to the CPU 300. If the reverse flag is set, the programmable control unit 100 controls the drill 102A or 102B to rotate the tool bit 150, 152, 154 or 156 in a direction that is opposite to the standard direction. At a process block 264, the CPU 300 loads a reverse motor speed value into the parameter control register. In one embodiment, as described above, the reverse motor speed value may be obtained from a dedicated row of the programming table. At a decision block 266, the CPU 300 determines whether the sequencer switch 138 has been pressed. The CPU 300 continues to execute the decision block 266 until the sequencer switch 138 is pressed. At this point, the CPU 300 advances to a process block 268. At the process block 268, the CPU 300 reloads the motor speed from the current gear ratio step of the programming table into the parameter control register. At a process block 270, the CPU 300 resets the internal reverse flag. After the process block 270, the CPU 300 returns to the decision block 244 of FIG. 13A.

A programming loop between the decision block 244 and either the decision block 260 or the process block 270 is continuously executed until either the manual-mode key 142C or the program-mode key 142B is pressed. The primary function of the run mode program is to provide preprogrammed desired values to the parameter control register as the surgeon steps through the rows of the programming table by pressing the sequencer switch 138 of the foot switch 104. These desired values in the parameter control register are utilized by a parameter control routine to achieve and maintain the desired values for the operating parameters of the drilling system 90. The parameter control routine is activated whenever the on/off switch 136 of the foot switch 104 is activated during either the run mode or the manual mode. At any specific time, the parameter control routine utilizes the current values that are placed into the parameter control register by either the run mode program or the manual mode program. The parameter control routine is described in greater detail below with reference to FIGS. 16A, 16B and 16C.

FIG. 14 is a flowchart illustrating the manual mode program for the CPU 300. The manual mode program begins at a block 272. At a decision block 274, the CPU 300 determines whether the run mode key 142A has been pressed. If the run mode key 142A has been pressed, the CPU 300 advances to a process block 276. Otherwise, the CPU 300 advances to a decision block 278. At the process block 276, the CPU 300 terminates execution of the manual mode program and begins to execute the run mode program that was described above with reference to FIGS. 13A and 13B.

At the decision block 278, the CPU 300 determines whether the up-arrow key 142E has been pressed. If the up-arrow key 142E has been pressed, the CPU 300 advances to a process block 280. Otherwise, the CPU 300 advances to a decision block 282. At the process block 280, the CPU 300 increments an active parameter value in the parameter control register by a predetermined amount. Each of the parameters that is controlled by the programmable control unit 200 is displayed on the LCD display 116. A cursor that is controlled by the CPU 300 indicates which parameter is currently active. If the rotational speed of the tool bit 150, 152, 154, or 156 is active, for example, the CPU 300 increments the speed by 10 revolutions per minute (rpm). After the process block 280, the CPU 300 advances to the decision block 282.

At the decision block 282, the CPU 300 determines whether the down-arrow key 142H has been pressed. If the down-arrow key 142H has been pressed, the CPU 300 advances to a process block 284. Otherwise, the CPU 300 advances to a decision block 286. At the process block 284, the CPU 300 decrements the active parameter value by a predetermined amount. For example, if the tool bit speed is the active parameter, the CPU 300 decrements the displayed value by 10 rpm. After the process block 284, the CPU 300 advances to the decision block 286.

At the decision block 286, the CPU 300 determines whether the left-arrow key 142G has been pressed. If the left-arrow key 142G has been pressed, the CPU 300 advances to a process block 288. Otherwise, the CPU 300 advances to a decision block 290. At the process block 288, the CPU 300 controls the cursor on the LCD display 116 to move to the left by one parameter. If the cursor is already at the leftmost parameter on the LCD display 116, the CPU 300 causes the cursor to wrap around to the rightmost parameter on the LCD display 116. After the process block 288, the CPU 300 advances to the decision block 290.

At the decision block 290, the CPU 300 determines whether the right-arrow key 142I has been pressed. If the right-arrow key 142I has been pressed, the CPU 300 advances to a process block 292. Otherwise, the CPU 300 returns to the decision block 274. At the process block 292, the CPU 300 causes the cursor on the LCD display 116 to move to the right by one parameter. If the cursor is at the rightmost parameter of the LCD display 116, the CPU 300 causes the cursor to wrap around to the leftmost parameter on the LCD display 116. After the process block 292, the CPU 300 returns to the decision block 274. The CPU 300 continues to execute the manual mode program until the run mode key 142A is pressed. The primary purpose of the manual mode program is to allow the surgeon to manually adjust the desired values that are provided to the parameter control routine through the parameter control register.

FIGS. 15A, 15B, 15C, 15D, and 15E form a flowchart illustrating the program mode program that is executed by the CPU 300. The program mode program begins at a block 320. At a process block 322, the CPU 300 displays the parameter values for the current gear ratio step in the programming table. These parameter values are displayed on the LCD display 116 and the LED display 118. At this point, there is no cursor active on the LCD display 116. At a decision block 324, the CPU 300 determines whether the run mode key 142A has been pressed. If the run mode key 142A has been pressed, the CPU 300 advances to a process block 326. Otherwise, the CPU 300 advances to a decision block 328. At the process block 326, the CPU 300 terminates execution of the program mode program and begins execution of the run mode program that was described above with reference to FIGS. 13A and 13B.

At the decision block 328, the CPU 300 determines whether the skip key 142D has been pressed. If the skip key 142D has been pressed, the CPU 300 advances to a process block 330. Otherwise, the CPU 300 advances to a decision block 332. At the process block 330, the CPU 300 sets the skip variable in the programming table for the current gear ratio step. When the skip variable for a gear ratio step is set, a surgeon will not have access to that gear ratio step when sequencing through the steps in the run mode. As described below, the skip variable for a gear ratio step can be reset by incrementing or decrementing the rotational speed of the tool bit 150, 152, 154 or 156 for the gear ratio step. After the process block 330, the CPU 300 advances to the decision block 332.

At the decision block 332, the CPU 300 determines whether the up-arrow key 142E has been pressed. If the up-arrow key 142E has been pressed, the CPU 300 advances to a process block 334. Otherwise, the CPU 300 advances to a decision block 336 of FIG. 15B. At the process block 334, the CPU 300 activates the previous gear ratio step in the programming table. Thus, for example, if the fourth gear ratio step is the current step, the CPU 300 activates the third gear ratio step to become the current gear ratio step. If the first gear ratio step is the current step, the CPU 300 activates the last gear ratio step to become the current step. After the process block 334, the CPU 300 advances to the decision block 336 of FIG. 15B.

At the decision block 336, the CPU 300 determines whether the down-arrow key 142H has been pressed. If the down-arrow key 142H has been pressed, the CPU 300 advances to a process block 338. Otherwise, the CPU 300 advances to a decision block 340. At the process block 338, the CPU 300 activates the next gear ratio step in the programming table. Thus, for example, if the fourth gear ratio step is the current step, the CPU 300 activates the fifth gear ratio step to become the current step. If the last gear ratio step is the current step, the CPU 300 activates the first gear ratio step to become the current step. After the process block 338, the CPU 300 advances to the decision block 340.

At the decision block 340, the CPU 300 determines whether the left-arrow key 142G has been pressed. If the left-arrow key 142G has been pressed, the CPU 300 advances to a decision block 342. Otherwise, the CPU 300 advances to a decision block 344. At the process block 342, the CPU 300 activates the cursor on the LCD display 116 at the rightmost parameter. After the process block 342, the CPU 300 advances to a decision block 348.

At the decision block 344, the CPU 300 determines whether the right-arrow key 142I has been pressed. If the right-arrow key 142I has not been pressed, the CPU 300 returns to the process block 322 of FIG. 15A. Otherwise, the CPU 300 advances to a process block 346. At the process block 346, the CPU 300 activates the cursor on the LCD display 116 at the leftmost parameter location. After the process block 346, the CPU 300 advances to the decision block 348.

Figure 15A:
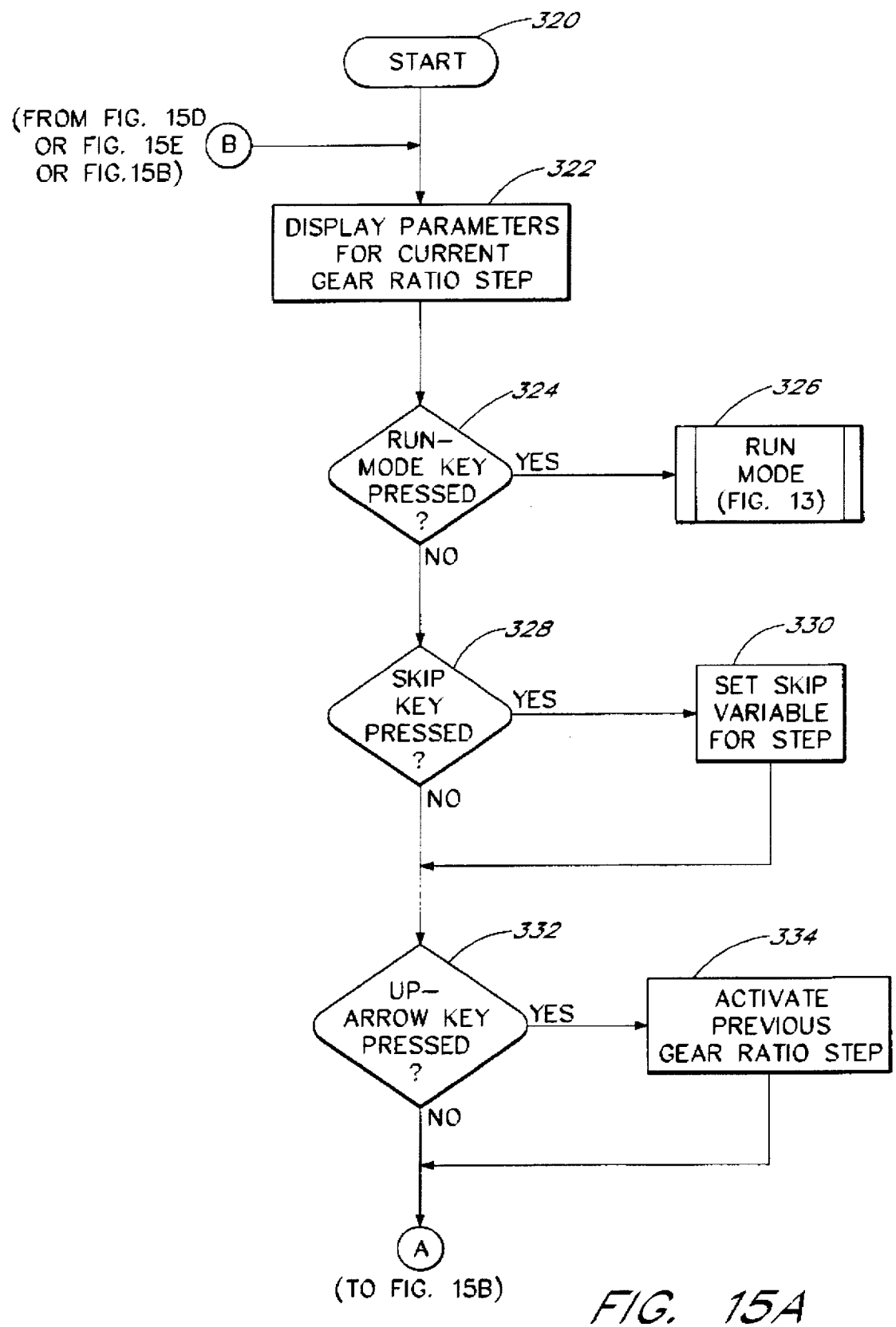
FIGS. 15A, 15B, 15C, 15D and 15E form a flowchart of a system level program mode program executed by a CPU of the programmable controller of FIG. 5.
Figure 15B:
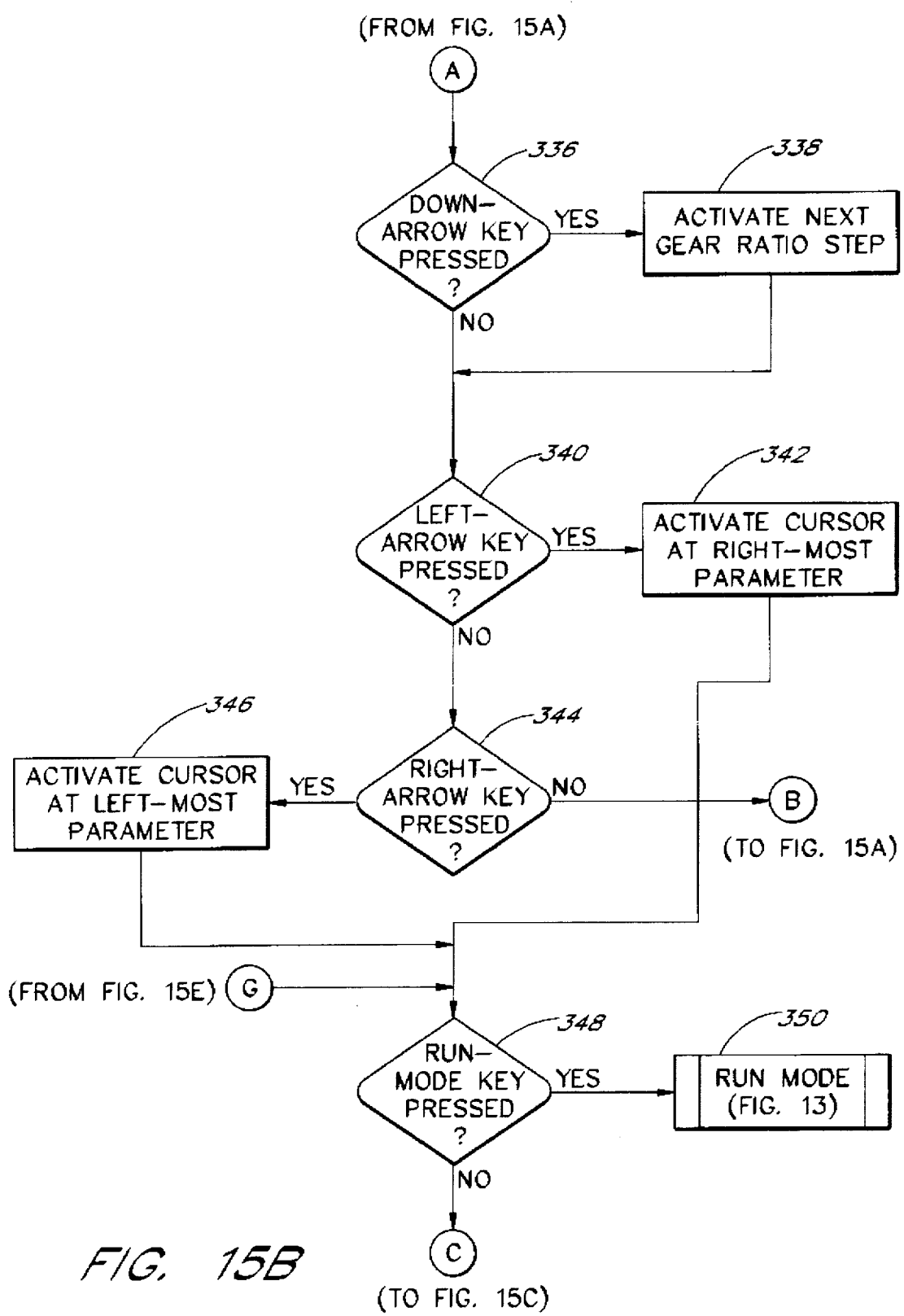
Figure 15C:
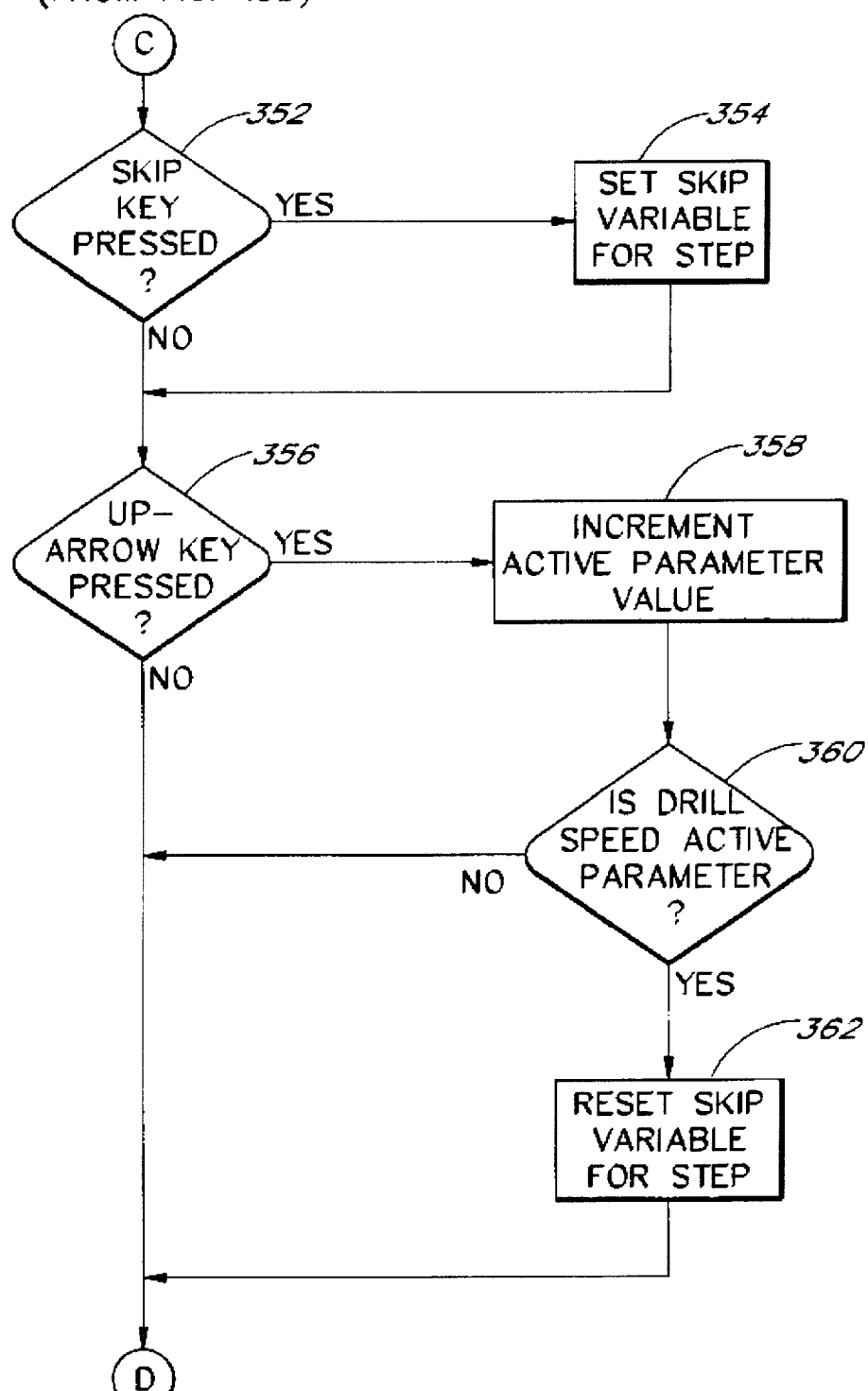
Figure 15D:
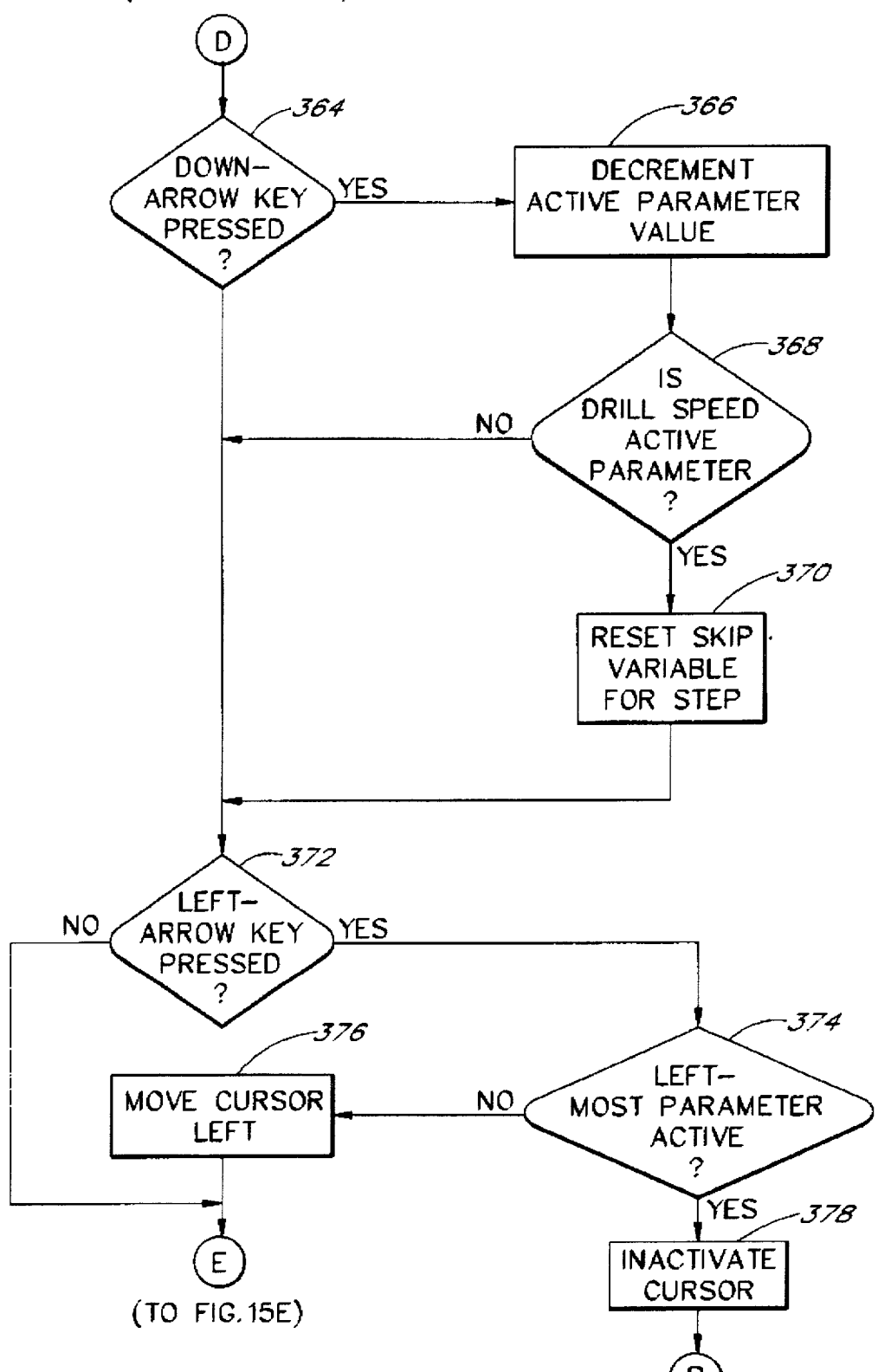

The CPU 300 continues to execute a program loop between the process block 322 of FIG. 15A and the decision block 344 of FIG. 15B until one of two events occur. The first event is for the operator to activate the run mode by pressing the run-mode key 142A. The second event is for the operator to activate the cursor on the LCD display 116 by pressing either the left-arrow key 142G or the right-arrow key 142-I. When this second event occurs, the CPU 300 advances to the decision block 348 to begin executing a separate program loop.

At the decision block 348, the CPU 300 determines whether the run mode key 142A has been pressed. If the run mode key 142A has been pressed, the CPU 300 advances to a process block 350. Otherwise, the CPU 300 advances to a decision block 352 of FIG. 15C. At the process block 350, the CPU 300 terminates execution of the program mode program and begins execution of the run mode program that was described above with reference to FIGS. 13A and 13B.

At the decision block 352, the CPU 300 determines whether the skip key 142D has been pressed. If the skip key 142D has been pressed, the CPU 300 advances to a process block 354. Otherwise, the CPU 300 advances to a decision block 356. At the process block 354, the CPU 300 sets the skip variable in the programming table corresponding to the current gear ratio step. After the process block 354, the CPU 300 advances to the decision block 356.

At the decision block 356, the CPU 300 determines whether the up-arrow key 142E has been pressed. If the up-arrow key 142E has been pressed, the CPU 300 advances to a process block 358. Otherwise, the CPU 300 advances to a decision block 364 of FIG. 15D. At the process block 358, the CPU 300 increments the active parameter value. This process block 358 is similar to the process block 280 of FIG. 14. After the process block 358, the CPU 300 advances to a decision bock 360. At the decision block 360, the CPU 300 determines whether the rotational speed of the tool bit 150, 152, 154 or 156 is the active parameter. If the rotational speed is the active parameter, the CPU 300 advances to a process block 362. Otherwise, the CPU 300 advances to the decision block 364 of FIG. 15D. At the process block 362, the CPU 300 resets the skip variable in the programming table corresponding to the current gear ratio step. After the process block 362, the CPU 300 advances to the decision block 364 of FIG. 15D.

At the decision block 364, the CPU 300 determines whether the down-arrow key 142H has been pressed. If the down-arrow key 142H has been pressed, the CPU 300 advances to a process block 366. Otherwise, the CPU 300 advances to a decision block 372. At the process block 362, the CPU 300 decrements the active parameter value. This process block 366 is similar to the process block 284 of FIG. 14. At a decision block 368, the CPU 300 determines whether the rotational speed of the tool bit 150, 152, 154 or 156 is the active parameter. If the rotational speed is not the active parameter, the CPU 300 advances to the decision block 372. Otherwise, the CPU 300 advances to a process block 370. At the process block 370, the CPU 300 resets the skip variable in the programming table corresponding to the current gear ratio step. After the process block 370, the CPU 300 advances to the decision block 372.

At the decision block 372, the CPU 300 determines whether the left-arrow key 142G has been pressed. If the left-arrow key 142G has been pressed, the CPU 300 advances to a decision block 374. Otherwise, the CPU 300 advances to a decision block 380 of FIG. 15E. At the decision block 374, the CPU 300 determines whether the cursor on the LCD display 116 is at the leftmost parameter location. If the cursor is at the leftmost parameter location, the CPU 300 advances to a process block 378. Otherwise, the CPU 300 advances to a process block 376. At the process block 378, the CPU 300 inactivates the cursor so that it no longer appears on the LCD display 116. After the process block 378, the CPU 300 returns to the process block 322 of FIG. 15A. At the process block 376, the CPU 300 moves the cursor on the LCD display 116 to the left by one parameter location. After the process block 376, the CPU 300 advances to the decision block 380 of FIG. 15E.

Figure 15E:
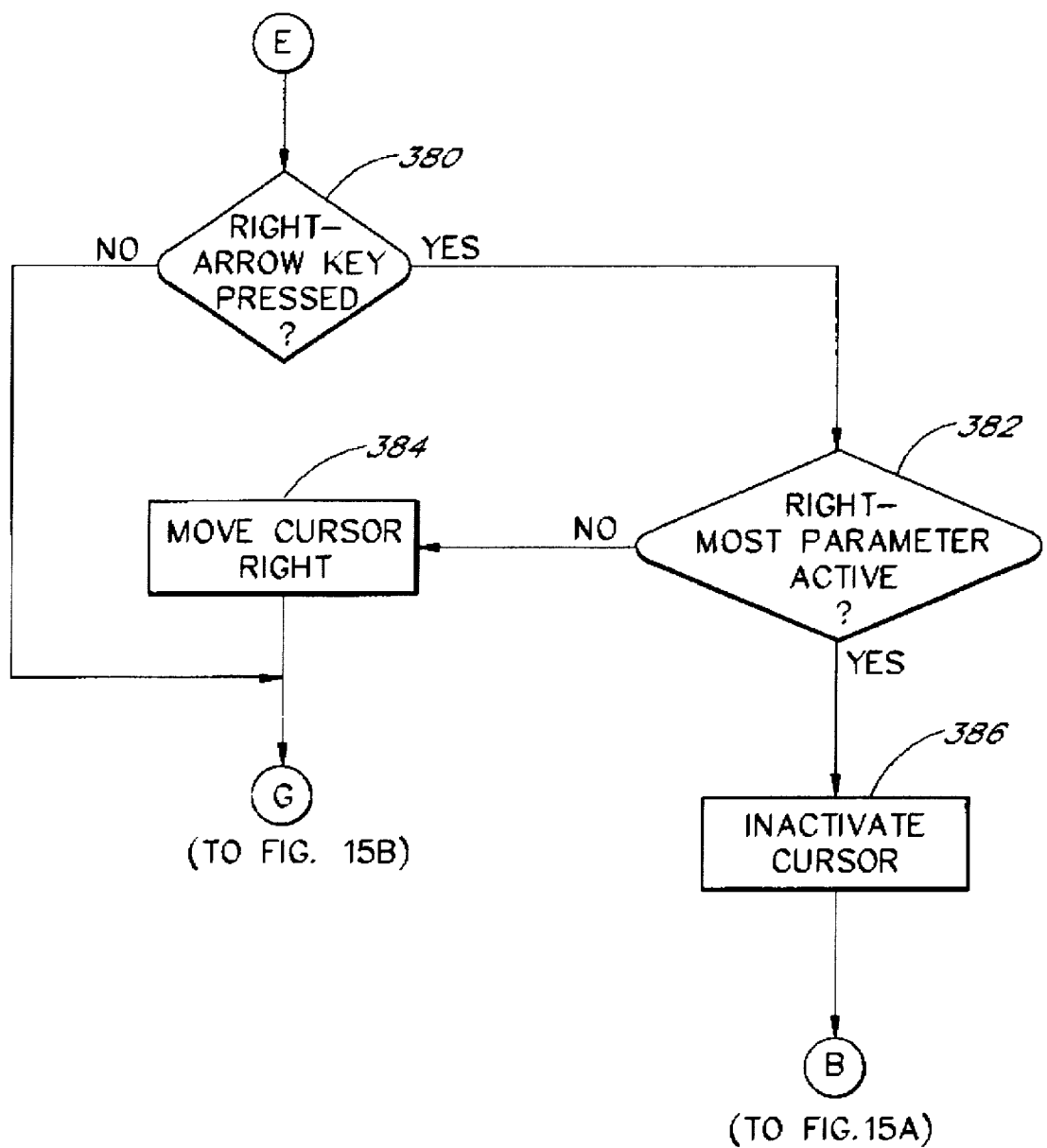

At the decision block 380 of FIG. 15E, the CPU 300 determines whether the right-arrow key 142I has been pressed. If the right-arrow key 142I has been pressed, the CPU 300 advances to a decision block 382. Otherwise, the CPU 300 returns to the decision block 348 of FIG. 15B. At the decision block 382, the CPU 300 determines whether the rightmost parameter on the LCD display 116 is active. If the rightmost parameter is active, the CPU 300 advances to a process block 386. Otherwise, the CPU 300 advances to a process block 384. At the process block 386, the CPU 300 inactivates the cursor so that it does not appear on the LCD display 116. After the process block 386, the CPU 300 returns to the process block 322 of FIG. 15A. At the process block 384, the CPU 300 moves the cursor on the LCD display 116 to the right by one parameter location. After the process block 384, the CPU 300 returns to the decision block 348 of FIG. 15B.

The CPU 300 continues to execute a program loop between the decision block 348 of FIG. 15B and the decision block 380 of FIG. 15E until one of two events occur. The first event is for the operator to activate the run mode by pressing the run-mode key 142A. The second event is for the operator to move the cursor off the LCD display 116 by pressing either the left-arrow key 142G or the right-arrow key 142I. When this second event occurs, the CPU 300 returns to the process block 322 of FIG. 15A to begin executing the previously described program loop of the program mode program.

Figure 16A:
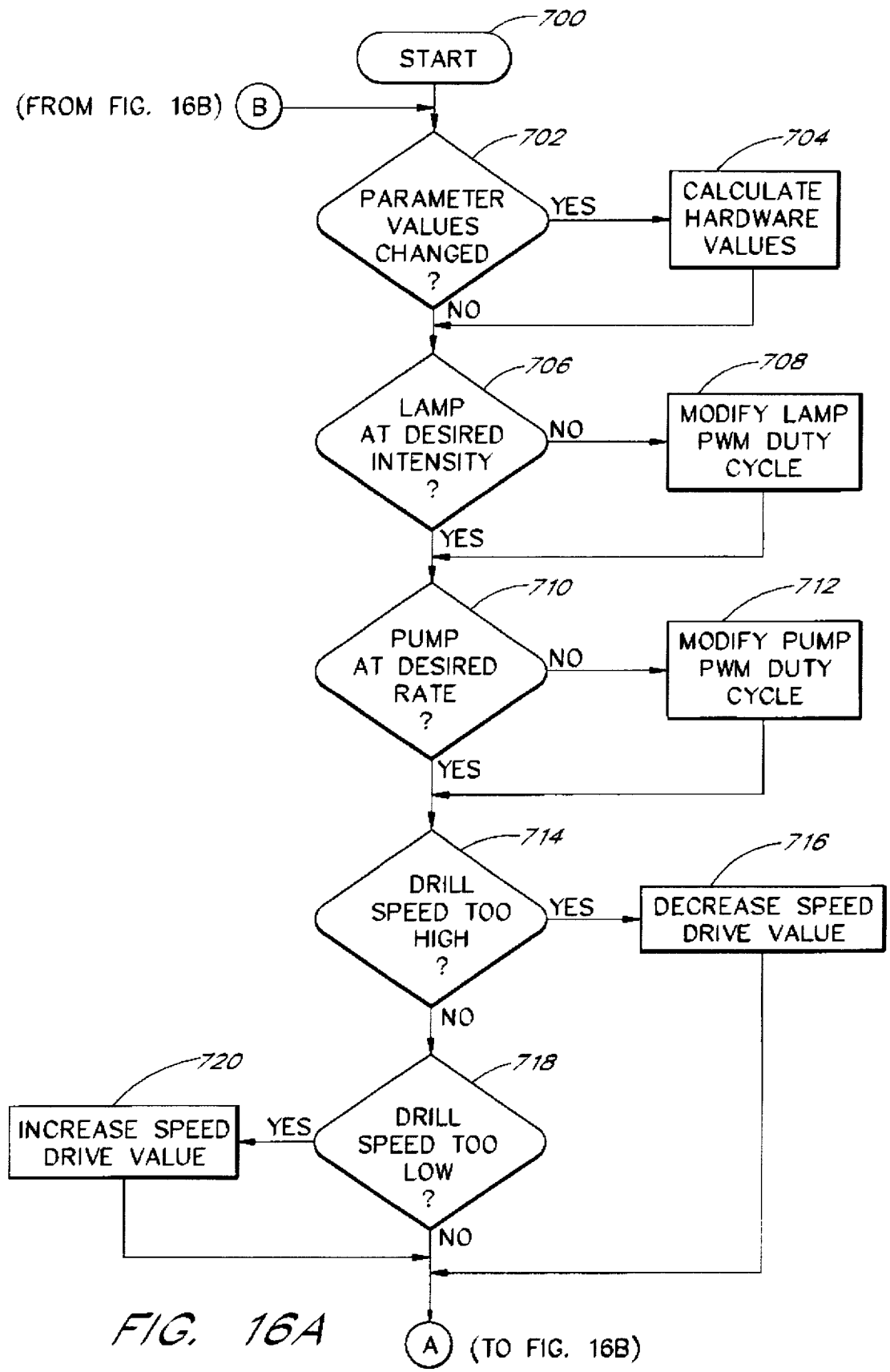
FIGS. 16A, 16B and 16C form a flowchart of a system level parameter control program executed by a CPU of the programmable controller of FIG. 5.
Figure 16B:
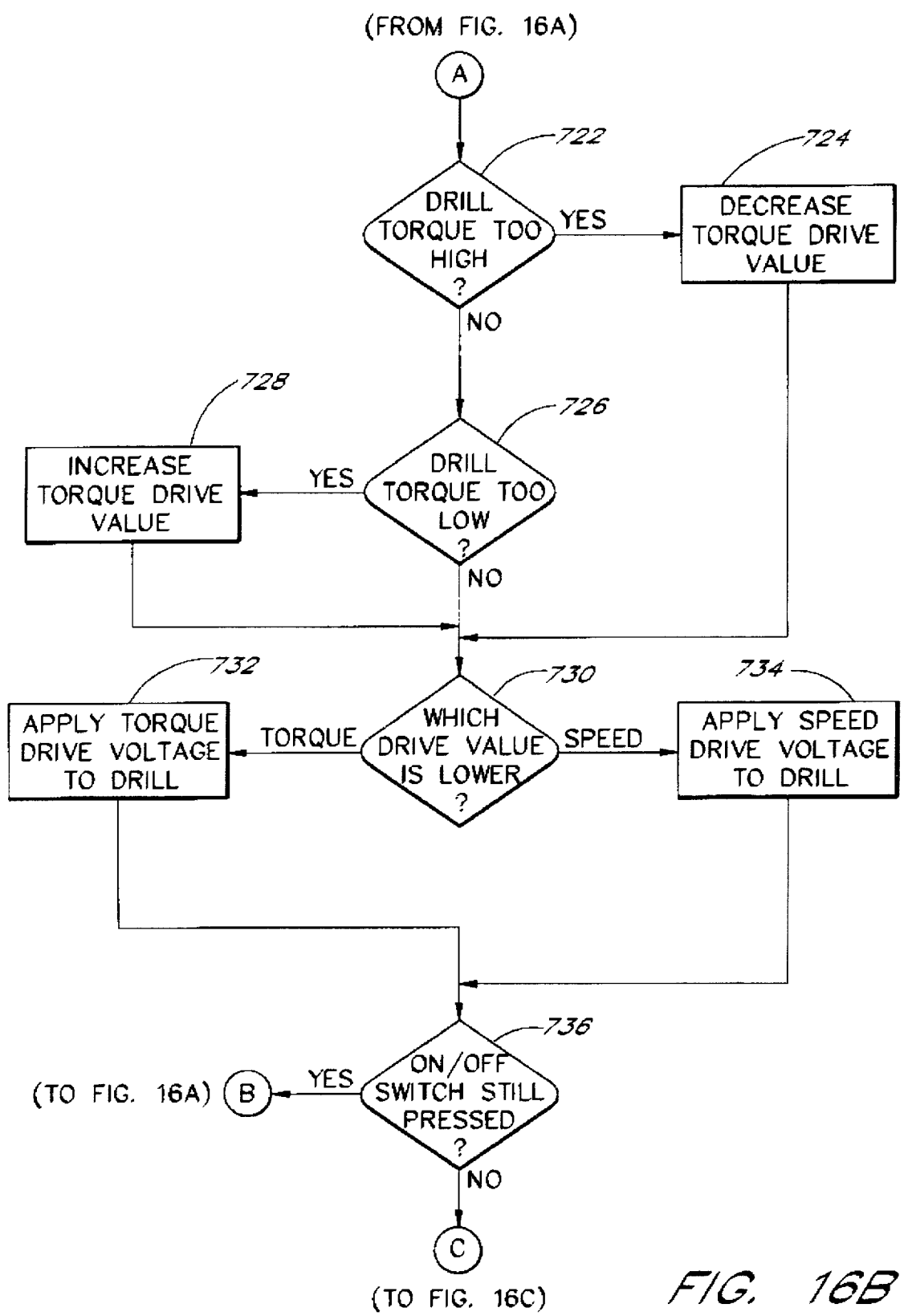
Figure 16C:
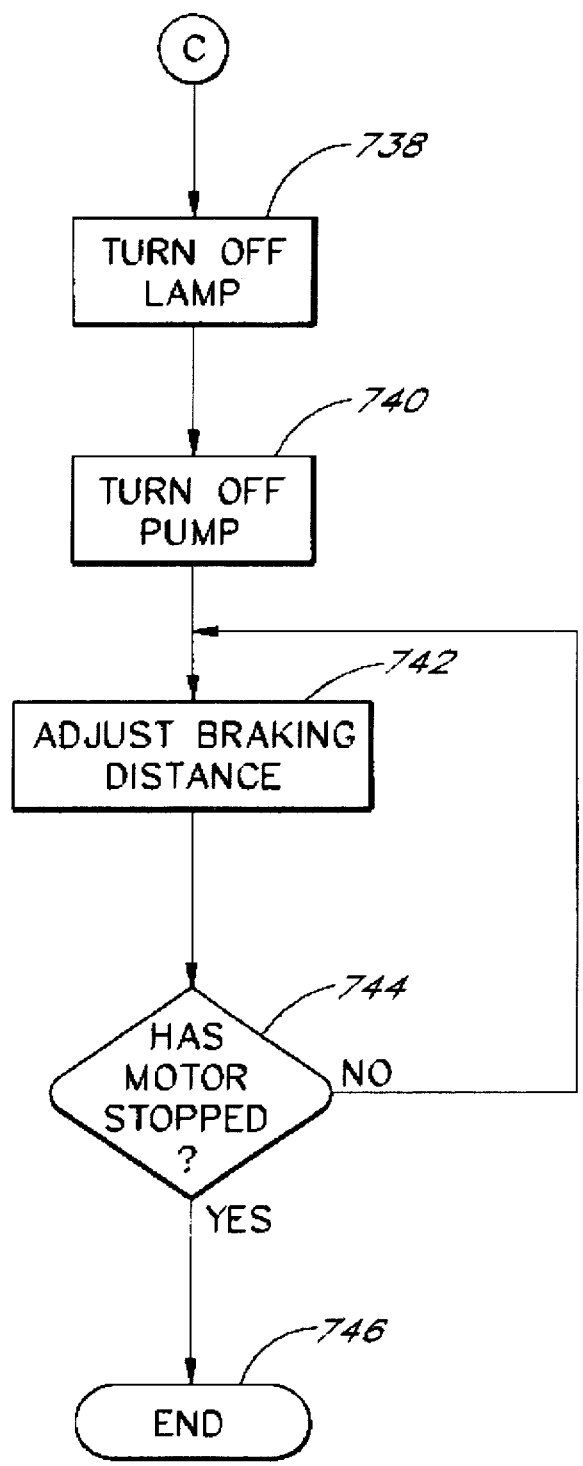

When the CPU 300 is in the program mode, the foot switch 104 is ignored. However, when the CPU 300 is in either the run mode or the manual mode, the foot switch 104 is operable. If the on/off switch 136 of the foot switch 104 is activated while the CPU 300 is in either the run mode or the manual mode, the programmable control unit 200 controls the operating parameters of the drilling system 90 to achieve and maintain the desired values indicated in the parameter control register. FIGS. 16A, 16B and 16C form a flowchart illustrating the parameter control routine executed by the CPU 300 to control the operating parameters of the drilling system 90 when the on/off switch 136 of the foot switch 104 is activated during either the run mode or the manual mode.

Referring to FIG. 16A, the parameter control routine begins at a block 700. At a process block 702, the CPU 300 determines whether the desired parameter values in the parameter control register have changed since the last time the decision block 702 was executed. During the first execution of the decision block 702, the CPU 300 concludes that the parameter values have been changed. If the parameters have been changed, the CPU 300 advances to a process block 704. Otherwise, the CPU 300 advances to a decision block 706. At the process block 704, the CPU 300 calculates a number of values that are required to control the operating parameters. For example, the CPU 300 calculates the motor current that corresponds to the desired torque value indicated in the parameter control register. After the process block 704, the CPU 300 advances to the decision block 706.

At the decision block 706, the CPU 300 determines whether the light source 144 is at the desired intensity represented in the parameter control register. This is determined by checking the duty cycle of the PWM signal on the light source PWM line 650 of FIG. 9. If the light source 144 is not being illuminated at the desired intensity, the CPU 300 advances to a process block 708. Otherwise, the CPU 300 advances to a decision block 710. At the process block 708, the CPU 300 modifies the duty cycle of the PWM signal on the light source PWM line 650. If the light source intensity is too low, the duty cycle of the PWM signal is increased. Otherwise, the duty cycle of the PWM signal is decreased. When initially illuminating the light source 144, the duty cycle of the PWM signal is set to, for example, just 10 percent of the duty cycle that is required to produce the desired intensity. During subsequent passes through the process block 708, the duty cycle of the PWM signal is gradually increased until the desired intensity is achieved. Thus, the CPU 300 performs a cold start of the light source 144. This gradual increase in the voltage applied across the light source 144 extends the useful life of most types of light sources 144. For example, a filament of an incandescent light bulb is likely to fail in a shorter period of time when it is routinely subjected to great increases in drive voltage. After the process block 708, the CPU 300 advances to the decision block 710.

At the decision block 710, the CPU 300 determines whether the pump 120 is generating the desired flow rate for the irrigation fluid. This condition is determined by checking the duty cycle of the PWM signal on the motor PWM line 550 of FIG. 7. If the desired flow rate has not been achieved, the CPU 300 advances to a process block 712. Otherwise, the CPU 300 advances to a decision block 714. At the process block 712, the CPU 300 modifies the duty cycle of the PWM signal on the motor PWM line 550. If the actual pump rate is lower than the desired pump rate, the CPU 300 increases the duty cycle of the PWM signal. If the actual pump rate is greater than the desired pump rate, the CPU 300 decreases the duty cycle of the PWM signal. The duty cycle of the PWM signal is modified by an amount that generates a difference in the drive voltage at the motor power line 558 that is within the tolerance of the pump 120. Thus, the process block 712 may be repeatedly executed during subsequent passes through the decision block 710, until the desired flow rate is achieved. After the process block 712, the CPU 300 advances to the decision block 714.

At the decision block 714, the CPU 300 begins to determine a new desired drive voltage to be applied to the motor power line 470 to control the drill 102A or 102B to achieve or maintain the desired values for the rotational speed and the torque at the tool bit 150, 152, 154 or 156. The CPU 300 calculates the required duty cycle at the motor PWM line 450 to achieve the desired drive voltage. A number of equations can be derived to calculate the desired drive voltage and the required duty cycle that depend on different hardware characteristics, such as characteristics of the motor 126A or 126B and characteristics of analog-to-digital converters and digital-to-analog converters. These characteristics can be determined by referring to manufacturers' data sheets or by electronic analysis.

Generally, the motor 126A or 126B has an effective motor resistance (R). The effective motor resistance may be, for example, 4 ohms. The actual voltage between the motor power line 470 and the motor return line 474 or 476 is a measured drive voltage ($V_M$). The actual current flowing through the motor 126A or 126B is a measured drive current ($I_M$). The measured drive voltage is generally equal to a back EMF voltage ($V_{EMF}$) added to the product of the effective motor resistance and the measured drive current ($V_M = V_{EMF} + I_M * R$). The torque at the tool bit 150, 152, 154 or 156 is generally a linear function of the measured drive current, while the rotational speed is generally a linear function of the back EMF voltage. The CPU 300 must calculate a drive current limit ($I_{LIM}$) that corresponds to the desired torque and a back EMF voltage limit ($V_{LIM}$) that corresponds to the desired rotational speed.

At the decision block 714, the CPU 300 determines whether the rotational speed of the tool bit 150, 152, 154 or 156 is greater than the desired rotational speed. This is accomplished by monitoring the voltage at the motor voltage line 482, which represents the measured drive voltage at the motor power line 470; and the current at the motor current line 484, which represents the measured drive current. The back EMF voltage is calculated using the following equation:

$$V_{EMF} = V_M - I_M * R$$

If the back EMF voltage is greater than the back EMF voltage limit, the rotational speed is too high. Under these circumstances, the CPU 300 advances to a process block 716. Otherwise, the CPU 300 advances to a decision block 718. At the process block 716, the CPU 300 decreases a speed drive value in a programming variable. The speed drive value represents a duty cycle that should be applied to the motor PWM line 450 to achieve a desired measured drive voltage, based on the actual rotational speed. The torque is not considered in making this determination. Generally, to achieve a desired rotational speed, the desired measured drive voltage should be calculated as follows:

$$V_M = V_{LIM} + I_M * R$$

After the process block 716, the CPU 300 advances to a decision block 722 of FIG. 16B.

At the decision block 718, the CPU 300 determines whether the actual drill speed is lower than the desired drill speed. This is accomplished by comparing the back EMF voltage against the back EMF voltage limit. If the back EMF voltage is less than the back EMF voltage limit, the CPU 300 advances to a process block 720. Otherwise, the CPU 300 advances to the decision block 722 of FIG. 16B. At the process block 720, the CPU 300 increases the speed drive value. Again, to achieve a desired rotational speed, the desired measured drive voltage should generally be calculated as follows:

$$V_M = V_{LIM} + I_M * R$$

However, in the preferred embodiment, the speed drive value is set to a lower value. For example, the speed drive value may be set to achieve a measured drive voltage of:

$$V_M = V_{EMF} + I_M * R + (V_{LIM} - V_{EMF})/3$$

Using this equation for the measured drive voltage gradually increases the rotational speed to the desired value. If the measured drive voltage were set to attempt to immediately achieve the desired rotational speed for an actual rotational speed that is either too high or too low, the actual rotational speed might oscillate too much around the desired value. The two equations for the desired measured drive voltage for a rotational speed that is either too high or too low may be modified to achieve different response characteristics for the drill 126A or 126B. The abovedescribed equations result in a quick response to an overspeed condition and a slower response to an under-speed condition. After the process block 720, the CPU 300 advances to the decision block 722 of FIG. 16B.

At the process block 722, the CPU 300 determines whether the torque at the tool bit 150, 152, 154, or 156 is greater than the desired torque. This is determined by monitoring the motor current line 484, which represents the measured drive current. If the measured drive current is greater than the drive current limit, the torque is greater than the desired value, and the CPU 300 advances to a process block 724. Otherwise, the CPU 300 advances to a decision block 726. At the process block 724, the CPU 300 decreases a torque drive value in a programming variable. The torque drive value represents a duty cycle that should be applied to the motor PWM line 450 to achieve a desired measured drive voltage, based on the actual torque. The rotational speed is not considered in making this determination. Generally, to achieve a desired torque, the desired measured drive voltage should be calculated as follows:

$$V_M = V_{EMF} + I_{LIM} * R$$

After the process block 724, the CPU 300 advances to a decision block 730.

At the decision block 726, the CPU 300 determines whether the actual torque is less than the desired torque. If the measured drive current is less than the drive current limit, the CPU 300 advances to a process block 728. Otherwise, the CPU 300 advances to the decision block 730. At the process block 728, the CPU 300 increases the torque drive value. Again, to achieve a desired torque, the desired measured drive voltage should generally be calculated as follows:

$$V_M = V_{EMF} + I_{LIM} * R$$

However, in the preferred embodiment, the torque drive value is set to a lower value. For example, the torque drive value may be set to achieve a measured drive voltage of:

$$V_M = V_{EMF} + I_M * R + R(I_{LIM} - I_M)/6$$

Using this equation for the measured drive voltage gradually increases the torque to the desired value. If the measured drive voltage were set to attempt to immediately achieve the desired torque whether the actual torque were too high or too low, the actual torque might oscillate too much around the desired value. The two equations for the desired measured drive voltage for a torque that is either too high or too low may be modified to achieve different response characteristics for the drill 126A or 126B. The above-described equations result in a quick response to an over-torque condition and a slower response to an under-torque condition. After the process block 728, the CPU 300 advances to the decision block 730.

At the decision block 730, the CPU 300 determines whether the speed drive value or the torque drive value is the lower value. If the speed drive value is lower than the torque drive value, the CPU 300 advances to a process block 734. Otherwise, the CPU 300 advances to a process block 732. At the process block 734, the CPU 300 sets the duty cycle of the PWM signal on the motor PWM line 450 according to the speed drive value. This modification to the duty cycle of the PWM signal on the motor PWM line 450 results in a change in the drive voltage at the motor power line 470. This results in an increased drive voltage or a decreased drive voltage, depending on whether the rotational speed is too low or too high, respectively. After the process block 734, the CPU 300 advances to a decision block 736. At the process block 732, the CPU 300 sets the duty cycle of the PWM signal on the motor PWM line 450 according to the torque drive value. This modification to the duty cycle of the PWM signal results in a change in the drive voltage at the motor power line 470. The drive voltage at the motor power line 470 is increased if the actual torque is lower than the desired torque, while the drive voltage at the motor power line 470 is decreased if the actual torque is higher than the desired torque. After the process block 732, the CPU 300 advances to the decision block 736.

At the decision block 736, the CPU 300 determines whether the on/off switch 136 of the foot switch 104 is still being pressed by the operator. If the on/off switch 136 is still being pressed, the CPU 300 returns to the decision block 702 of FIG. 16A. Otherwise, the CPU 300 advances to a process block 738 of FIG. 16C.

At the process block 738, the CPU 300 turns off the light source 144 by disabling the PWM signal on the light source PWM line 650. At a process block 740, the CPU 300 turns off the pump 120 by disabling the PWM signal on the motor PWM line 550. At a process block 742, the CPU 300 applies or adjusts a braking resistance that is between the motor power line 470 and the motor return line 474 or 476. As described above with reference to FIG. 6, the resistance supplied across the terminals of the motor 126A or 126B is determined by the duty cycle of the PWM signal on the brake PWM line 452. An applied braking resistance is selected that maximizes the power dissipation of the brake driver 408 of FIG. 6. The power dissipated by the brake driver 408 is determined by multiplying the applied braking resistance by the square of the current flowing through the motor 126A or 126B. The current flowing through the motor 126A or 126B is determined by monitoring the motor current line 484. After the process block 742, the CPU 300 advances to a decision block 744. At the decision block 744, the CPU 300 determines whether the motor 126A or 126B has stopped rotating the tool bit 150, 152, 154, or 156. This condition is determined by monitoring the motor voltage line 482, which represents the voltage at the motor power line 470. If the voltage at the motor power line 470 is zero, the motor has stopped. If the motor has not stopped, the CPU 300 returns to the process block 742. Otherwise, the CPU 300 advances to a block 746. At the block 746, execution of the program represented by FIGS. 16A, 16B, and 16C is terminated.

What is claimed:

1. An apparatus for performing a surgical procedure comprising a plurality of steps, each of said steps involving the use of said apparatus on hard tissue in accordance with selected operating parameters, said apparatus comprising a drill comprising a motor, a handpiece, and a tool, said motor driving said tool upon activation of said motor, said apparatus further comprising:

means for inputting a first set of data values representing the magnitudes of said operating parameters for one of said plurality of steps of said surgical procedure;

means for inputting a second set of data values representing the magnitudes of said operating parameters for another of said plurality of steps of said surgical procedure;

means for concurrently storing said first and second sets of data values;

means for selectively recalling any one of said concurrently stored sets of data values;

means for causing said drill to operate in accordance with the parameter magnitudes corresponding to each of the recalled set of data values, said means for causing said apparatus to operate comprising:

means for monitoring the magnitude of at least a selected operational parameter during operation of said apparatus; and means for controlling the magnitude of said selected operational parameter, said means for controlling being responsive to said means for monitoring to substantially maintain the magnitude of the selected operational parameter at a value corresponding to the value represented by the recalled set of data values.

2. The apparatus of claim 1, wherein said tool comprises a tool bit and wherein said selected operational parameter is the rotational speed of the tool bit.

3. The apparatus of claim 1, wherein said tool comprises a tool bit and wherein said selected operational parameters of said apparatus comprise a rotational speed of a tool bit, a torque of said tool bit, and a rotational direction of said tool bit.

4. The apparatus of claim 3, wherein said selected operational parameter monitored by said means for monitoring comprises torque applied to said tool bit.

5. The apparatus of claim 3, wherein said means for controlling and said means for monitoring comprise a microprocessor.

6. The apparatus of claim 5, wherein said means for controlling comprises a motor driver for applying a voltage to the drill motor and a brake driver for applying a resistance to the drill motor, said motor driver and said brake driver controlling said rotational speed of said tool bit.

7. The apparatus of claim 4, wherein said tool bit comprises a screw drive.

8. The apparatus of claim 1, additionally comprising a cable connected to said drill, wherein said means for causing said apparatus to operate comprises means electrically connected to said cable for applying a drive voltage across said motor of said drill to activate said motor, wherein said monitoring means comprises means for determining the drive voltage applied across said motor and means for determining the current flowing through said motor and wherein said controlling means comprises means for adjusting said drive voltage applied across said motor to adjust the magnitude of said selected operational parameter.

9. The apparatus of claim 8, wherein said tool comprises a rotatable tool bit and wherein said handpiece comprises a gear train having a gear ratio, said controlling means additionally comprising:

means for calculating the torque applied to said tool bit using the actual current flowing through said motor and the gear ratio of said gear train; and means for calculating the rotational speed of said tool bit using the actual drive voltage applied across said motor and the gear ratio of said gear train.

10. The apparatus of claim 9, wherein said means for calculating the rotational speed and said means for adjusting said drive voltage comprise a microprocessor and wherein said means for storing said plurality of data values comprises an EEPROM.

11. The apparatus of claim 8, wherein said controlling means additionally comprises means for applying a braking resistance across said motor to absorb energy of the moving tool and thereby rapidly slow the motion of said tool.

12. The apparatus of claim 11, wherein said applying means comprises a switching power regulator utilizing a pulse width modulation signal.

13. The apparatus of claim 1, additionally comprising means for supplying a DC voltage for lighting a light bulb, said supplying means producing a pulse width modulation signal duty cycle which increases over time from a minimum to a maximum, and means for converting said pulse width modulation signal to said DC voltage for lighting said light bulb, whereby the amount of voltage supplied to said light bulb is gradually increased to reduce voltage-induced stress on the filament of the light bulb.

14. The apparatus of claim 8, wherein said monitoring means monitors first and second operational parameters, said adjusting means changing the drive voltage so that (i) the magnitudes of said first and second optional parameters are substantially at or beneath first and second desired maximum values, respectively, and (ii) the magnitude of at least one of said first and second operational parameters is substantially at its desired maximum value.

15. The apparatus of claim 14, wherein said adjusting means changes the drive voltage in accordance with a selected one of four different functions, the selected function depending on which, if any, of said first and second operational parameters have magnitudes that exceed the first and second desired maximum values, respectively, and which, if any, of said first and second operational parameters have magnitudes that are less than the first and second desired maximum values, respectively.

16. The apparatus of claim 15, wherein said first operational parameter is the speed of the tool and said second operational parameter is the torque on said tool.

17. The apparatus of claim 16, wherein said applying means comprises a switching power regulator utilizing pulse width modulation, said power regulator producing said drive voltage as a function of said pulse width modulation, said adjusting means utilizing the selected one of said four functions to control said pulse width modulation and thereby control said drive voltage on said motor.

* * * * *

UNITED STATES PATENT AND TRADEMARK OFFICE
CERTIFICATE OF CORRECTION

PATENT NO. : 5,538,423
DATED : July 23, 1996
INVENTOR(S) : Ronald G. Coss and James H. Dabney It is certified that error appears in the above-indentified patent and that said Letters Patent is hereby corrected as shown below:

At Column 30, Line 15, please change "screw drive" to

--screw driver--.

Signed and Sealed this

Twenty-first Day of January, 1997

Attest:

BRUCE LEHMAN

*Attesting Officer*  *Commissioner of Patents and Trademarks*